United States Patent [19]
Pavlov et al.

[11] Patent Number: 5,906,616
[45] Date of Patent: May 25, 1999

[54] CONICALLY SHAPED ANTERIOR FUSION CAGE AND METHOD OF IMPLANTATION

[75] Inventors: Paul W. Pavlov, Nijmegen, Netherlands; Charles J. Winslow, Walnut Creek, Calif.; Kirk Jayne, Alameda, Calif.; Henry A. Klyce, Piedmont, Calif.

[73] Assignee: Surgical Dynamics, Inc., Norwalk, Conn.

[21] Appl. No.: 08/783,790

[22] Filed: Jan. 15, 1997

Related U.S. Application Data

[63] Continuation of application No. 08/354,364, Dec. 12, 1994, abandoned, which is a continuation-in-part of application No. 08/306,879, Sep. 15, 1994, abandoned.

[51] Int. Cl.$^6$ ....................................................... A61B 17/56
[52] U.S. Cl. ................................................. 606/61; 623/17
[58] Field of Search .................................. 606/61, 60, 72, 606/73, 76, 77, 65, 66, 90, 104; 623/16, 17

[56] References Cited

U.S. PATENT DOCUMENTS

| | | |
|---|---|---|
| 3,298,372 | 1/1967 | Feinberg . |
| 3,486,505 | 12/1969 | Morrison . |
| 3,719,186 | 3/1973 | Merig, Jr. . |
| 3,867,728 | 2/1975 | Stubstad et al. . |
| 3,871,031 | 3/1975 | Boutin . |
| 3,906,550 | 9/1975 | Rostoker et al. . |
| 3,986,212 | 10/1976 | Sauer . |
| 4,013,071 | 3/1977 | Rosenberg . |
| 4,016,651 | 4/1977 | Kawahara et al. . |
| 4,086,701 | 5/1978 | Kawahara et al. . |
| 4,124,026 | 11/1978 | Berner et al. . |
| 4,177,524 | 12/1979 | Grell et al. . |
| 4,185,383 | 1/1980 | Heimke et al. . |
| 4,259,072 | 3/1981 | Hirabayashi et al. . |
| 4,349,921 | 9/1982 | Kuntz . |

(List continued on next page.)

FOREIGN PATENT DOCUMENTS

| | | |
|---|---|---|
| 2015507 | 12/1974 | Canada . |
| 0551187 | 7/1993 | European Pat. Off. . |
| 0637440 | 2/1995 | European Pat. Off. . |
| 2710519 | 4/1995 | France . |
| 1961531 | 9/1970 | Germany . |
| 4302397 | 7/1993 | Germany . |
| 4323595 | 7/1994 | Germany . |
| 8707827 | 12/1987 | WIPO . |
| 9417759 | 8/1994 | WIPO . |

OTHER PUBLICATIONS

Norman W. Hoover, M.D., "Methods of Lumbar Fusion", The Journal of Bone and Joint Surgery, Jan. 1968, pp. 192–210.

Shun–Ichi Inque, M.D., Ph.D., et al., "Anterior Discectomy and Interbody Fusion for Lumbar Disc Herniation", Lumbar Disc Herniation, vol. 183, Mar. 1984, pp. 22–31.

A. Kumar, M.D., et al., "Interspace Distraction and Graft Subsidence After Anterior Lumbar Fusion With Femoral Strut Allograft", SPINE vol. 18, No. 16, pp. 2392–2400, 1993.

Charles V. Burton, "Fusion: Where It's Been and Where It's Going", The International Society for the Study of the Lumbar Spine, The Lumbar Spine, Chapter 23, pp. 998–1003, 1993.

(List continued on next page.)

*Primary Examiner*—Guy V. Tucker

[57] ABSTRACT

A fusion cage for vertebral body fusion is conically-shaped. A thread is formed as part of the external conical surface of the fusion cage. Apertures are defined through the fusion cage in order to provide for contact between the engaged vertebral bone structures and bone growth inducing substances packed within the fusion cage. The fusion cage is introduced and maintains or increases the lordosis between adjacent vertebral bone structures.

40 Claims, 15 Drawing Sheets

U.S. PATENT DOCUMENTS

| | | | |
|---|---|---|---|
| 4,406,623 | 9/1983 | Grafelmann et al. . | |
| 4,468,200 | 8/1984 | Münch . | |
| 4,501,269 | 2/1985 | Bagby . | |
| 4,511,336 | 4/1985 | Hidaka et al. . | |
| 4,522,200 | 6/1985 | Stednitz . | |
| 4,525,145 | 6/1985 | Scheicher et al. . | |
| 4,537,185 | 8/1985 | Stednitz | 606/73 X |
| 4,545,374 | 10/1985 | Jacobson . | |
| 4,549,319 | 10/1985 | Meyer . | |
| 4,569,338 | 2/1986 | Edwards . | |
| 4,573,448 | 3/1986 | Kambin . | |
| 4,599,084 | 7/1986 | Nashef . | |
| 4,653,486 | 3/1987 | Coker . | |
| 4,673,409 | 6/1987 | Van Kampen | 623/23 |
| 4,725,280 | 2/1988 | Laure | 623/21 |
| 4,743,260 | 5/1988 | Burton | 623/17 |
| 4,759,768 | 7/1988 | Hermann et al. | 623/21 |
| 4,834,757 | 5/1989 | Brantigan | 623/17 |
| 4,863,430 | 9/1989 | Klyce et al. | 604/164 |
| 4,877,020 | 10/1989 | Vich . | |
| 4,904,261 | 2/1990 | Dove et al. | 623/17 |
| 4,927,421 | 5/1990 | Goble et al. | 606/73 |
| 4,936,848 | 6/1990 | Bagby | 623/17 |
| 4,936,851 | 6/1990 | Fox et al. | 623/16 |
| 4,950,270 | 8/1990 | Bowman et al. | 606/72 |
| 4,961,740 | 10/1990 | Ray et al. | 606/61 |
| 5,015,247 | 5/1991 | Michelson | 606/61 |
| 5,015,255 | 5/1991 | Kuslich . | |
| 5,026,373 | 6/1991 | Ray et al. | 606/61 |
| 5,055,104 | 10/1991 | Ray | 606/61 |
| 5,059,193 | 10/1991 | Kuslich . | |
| 5,062,845 | 11/1991 | Kuslich et al. . | |
| 5,134,499 | 7/1992 | Small et al. | 606/73 |
| 5,147,402 | 9/1992 | Bohler et al. . | |
| 5,195,541 | 3/1993 | Obenchain . | |
| 5,263,953 | 11/1993 | Bagby . | |
| 5,300,076 | 4/1994 | Leriche | 606/73 |
| 5,313,962 | 5/1994 | Obenchain . | |
| 5,354,292 | 10/1994 | Braeuer et al. . | |
| 5,354,302 | 10/1994 | Ko . | |
| 5,357,983 | 10/1994 | Mathews . | |
| 5,423,817 | 6/1995 | Lin . | |
| 5,425,772 | 6/1995 | Brantigan | 623/17 |
| 5,425,773 | 6/1995 | Boyd | 623/17 |
| 5,439,464 | 8/1995 | Shapiro . | |
| 5,445,639 | 8/1995 | Kuslich et al. . | |
| 5,458,638 | 10/1995 | Kuslich et al. . | |
| 5,484,437 | 1/1996 | Michelson . | |
| 5,489,308 | 2/1996 | Kuslich et al. . | |

OTHER PUBLICATIONS

Keith H. Bridwell, M.D., "Normal Sagittal Alignment", Federation of Spine Associations, Section IV—Scoliosis Research Society, Sagittal Spinal Balance—Symposium No. 1, Feb. 27, 1994.

Charles G. Hutter, "A Technique for Posterior Lumbar Interbody Fusion", Chapter 19, Lumbar Interbody Fusion, 1989, pp. 227–232.

S+G Implants, S+G Spongiosametall Lübeck, Blöcke Typ Waisbrod, 2 pages, Author and Date Unknown.

S+G Implants, S+G Cast Cancellous Metal, PLIF (Posterior Lumbar Interbody Fusion) with Cast Cancellous Metal Mould (CCMM), 4 pages.

Cage CR, Cerivical Spacing Cages, Cages Intersomatiques Cervicales, Scient'x, Paris, 1 page.

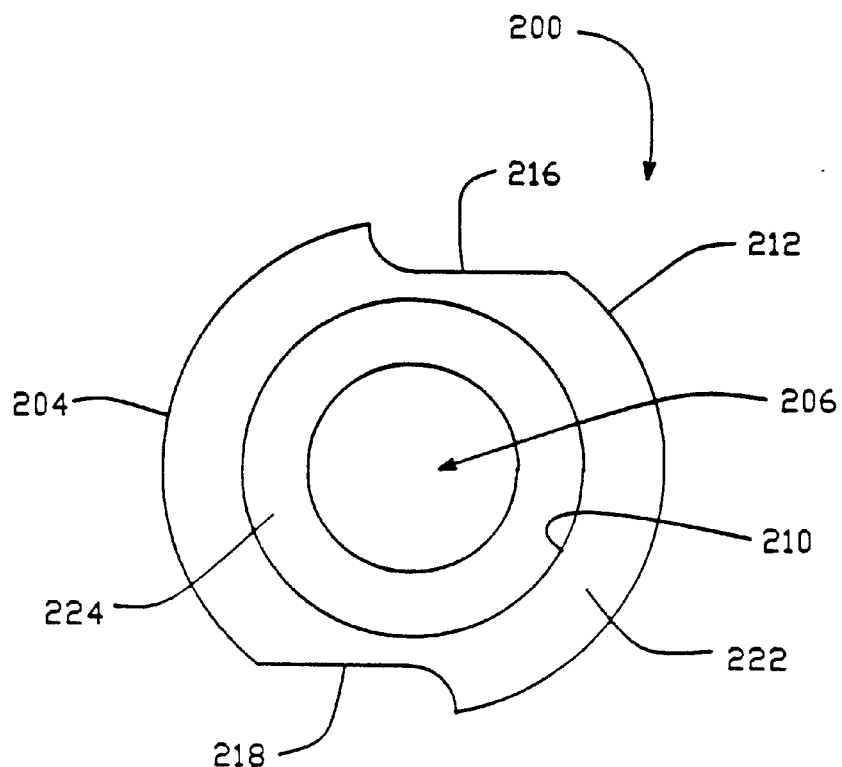
FIG.—12
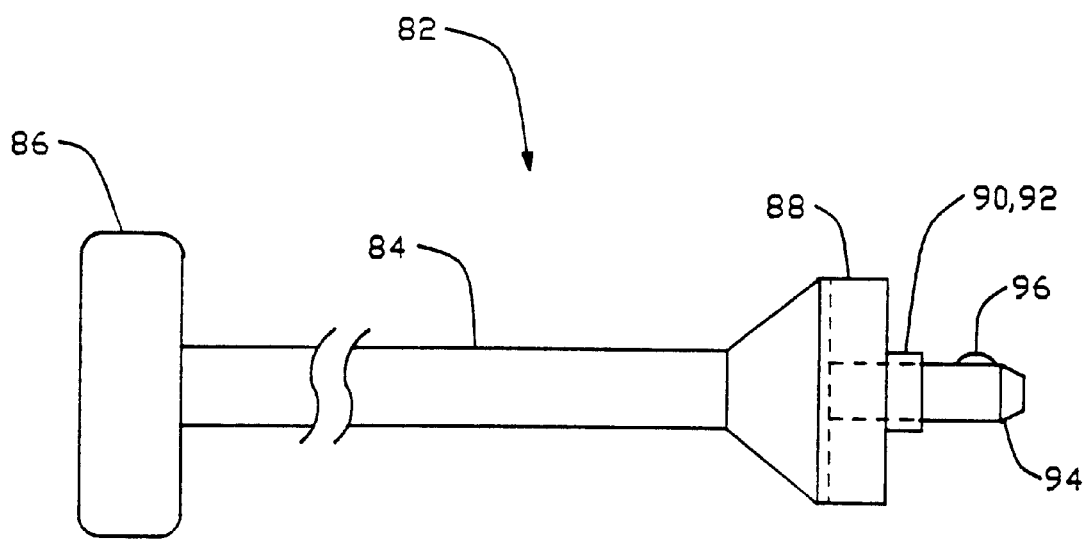
FIG.—6

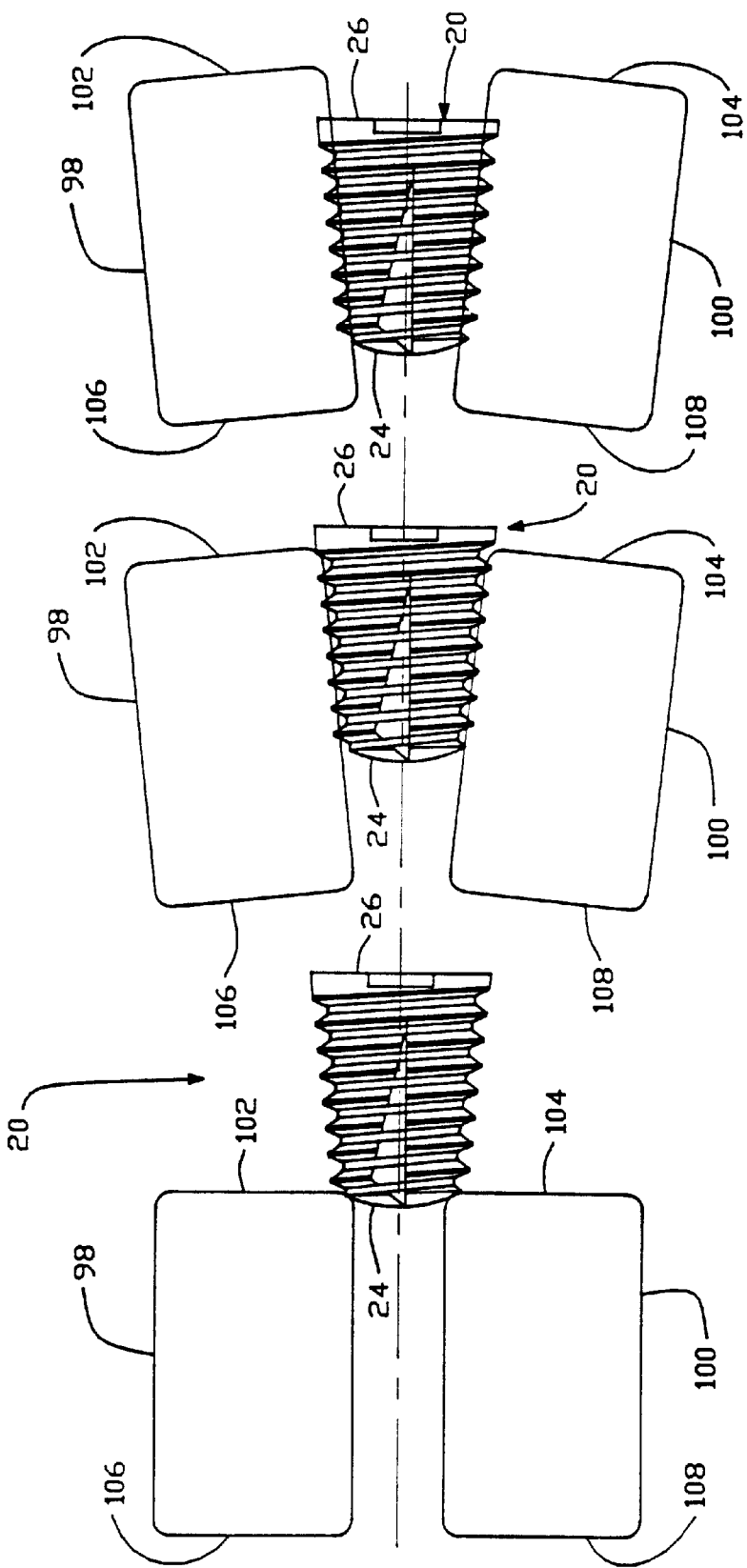

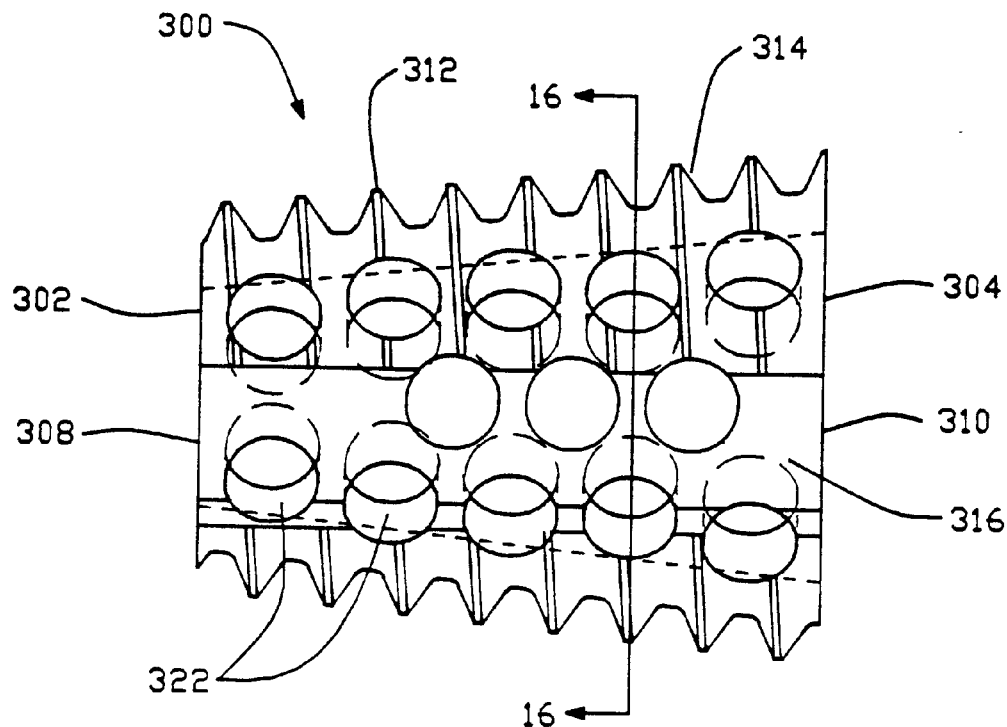
FIG.—13
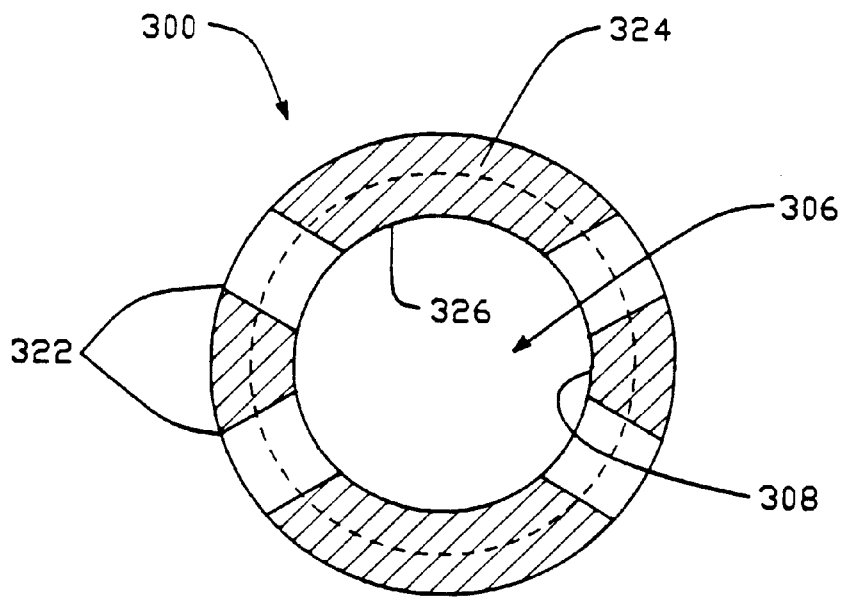
FIG.—16

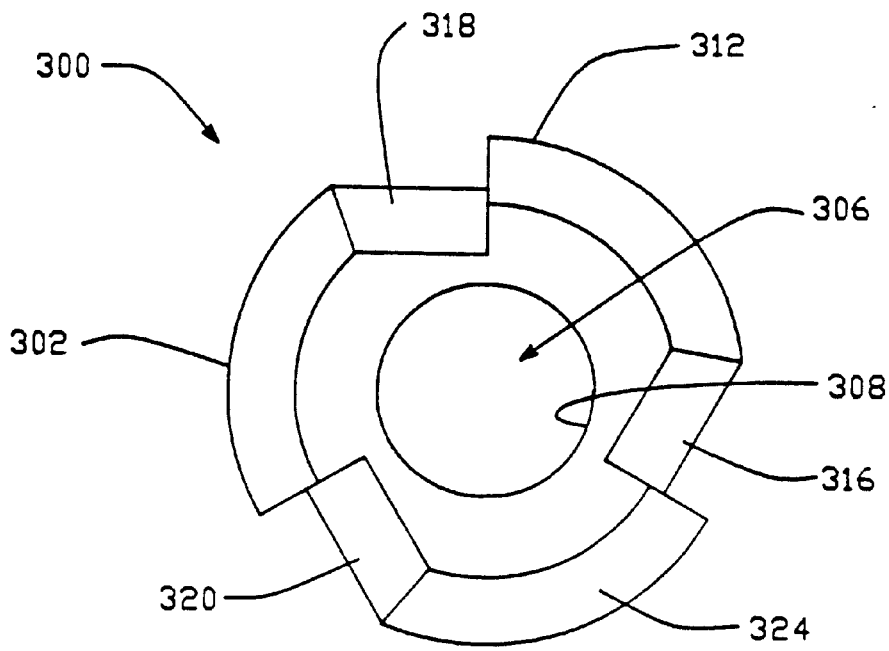
FIG.—14
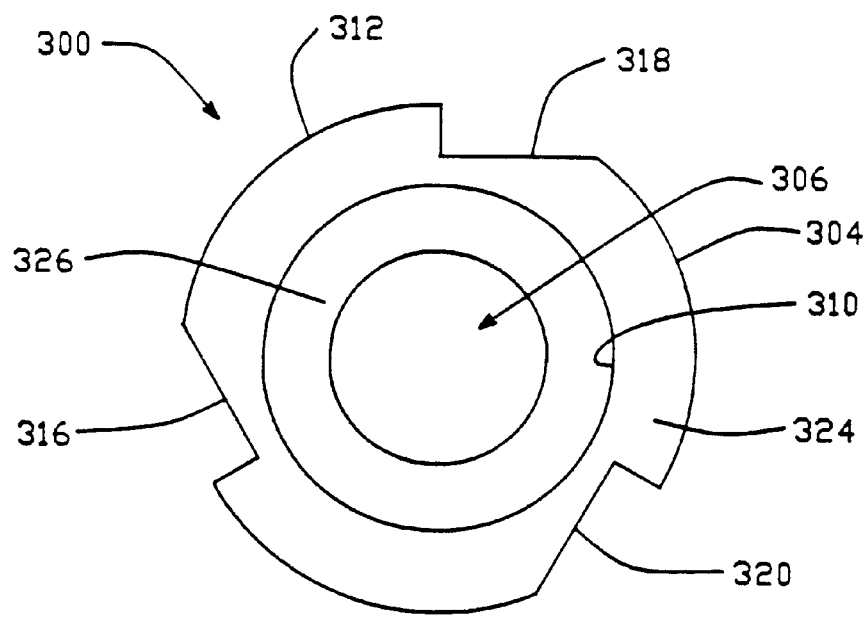
FIG.—15

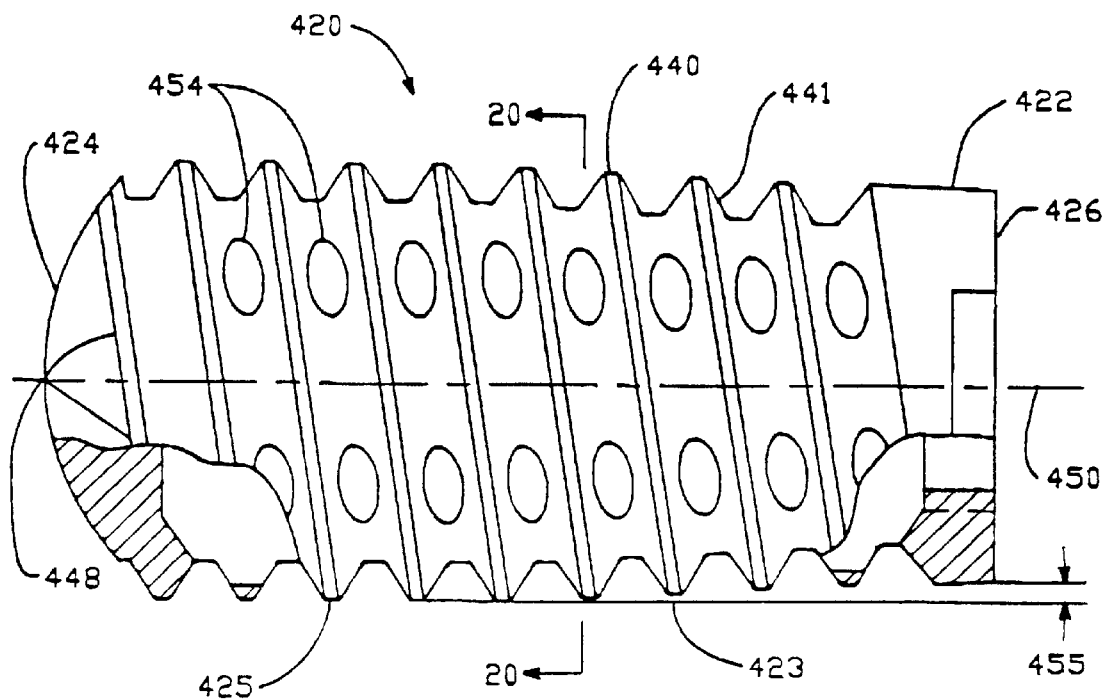
FIG.—17
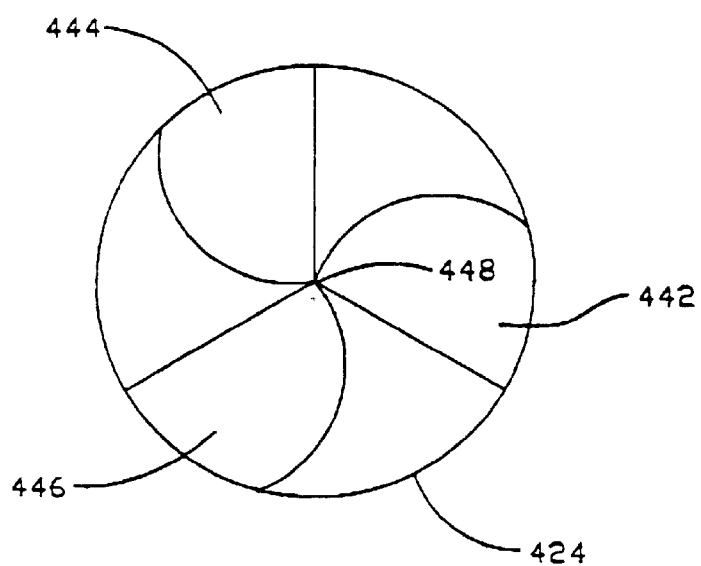
FIG.—18

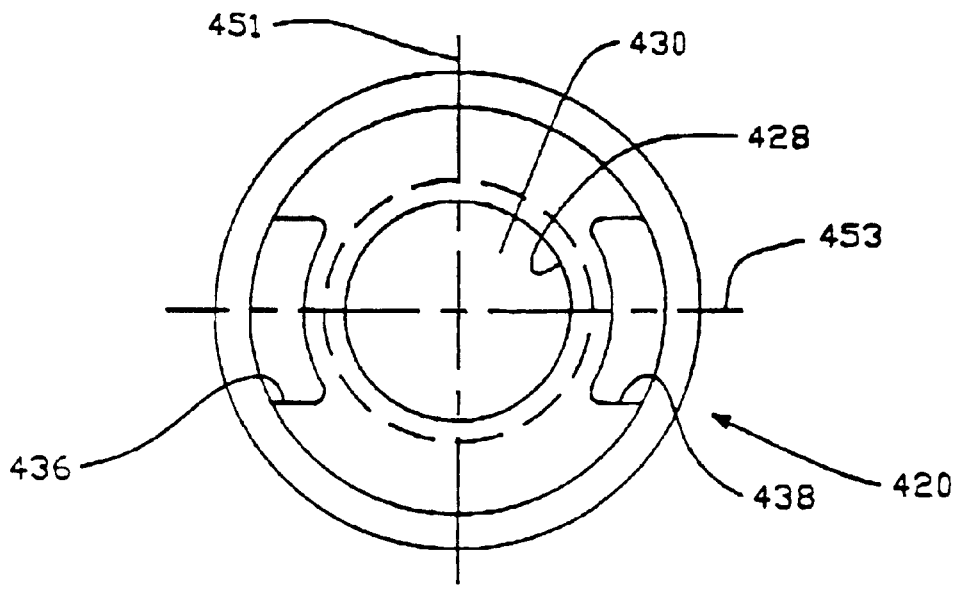
FIG.—19
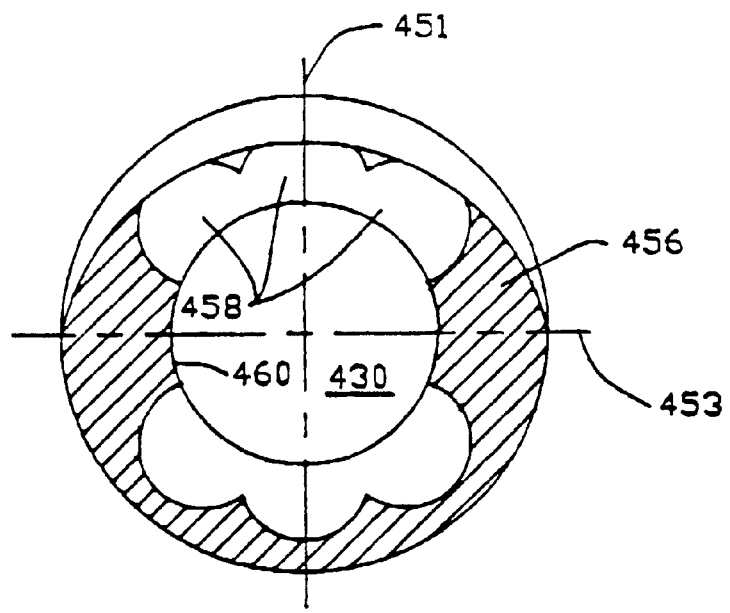
FIG.—20

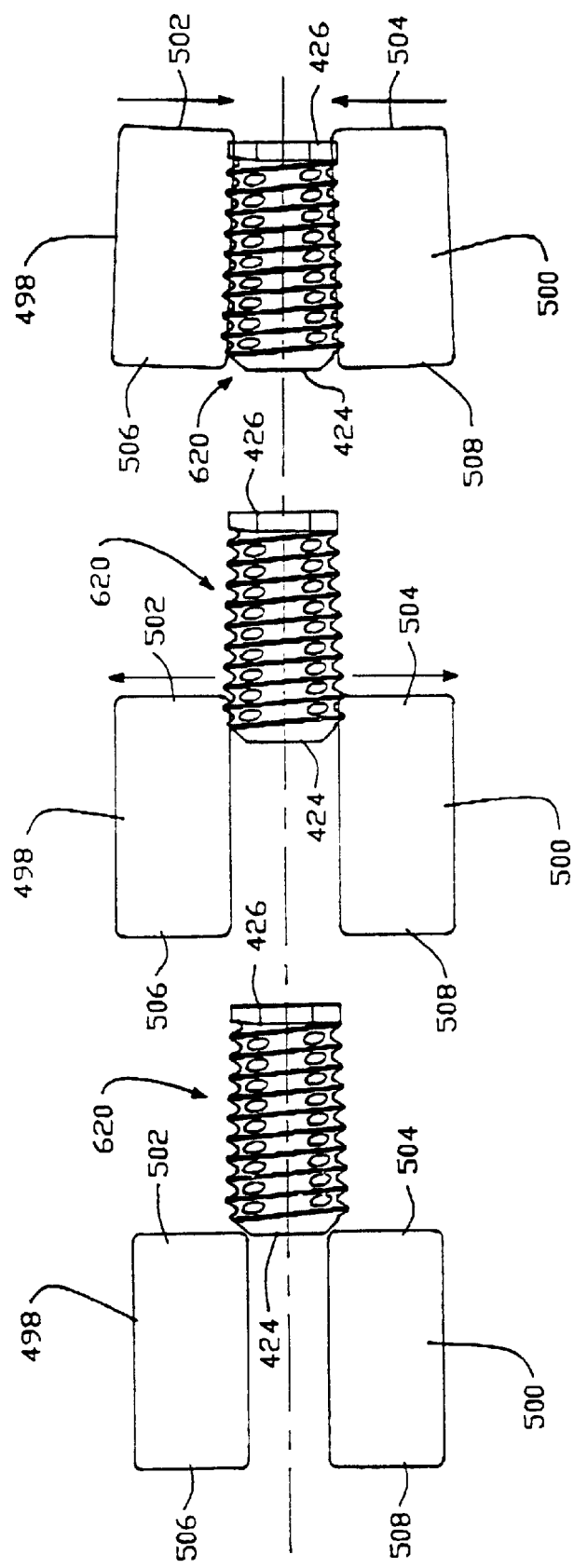

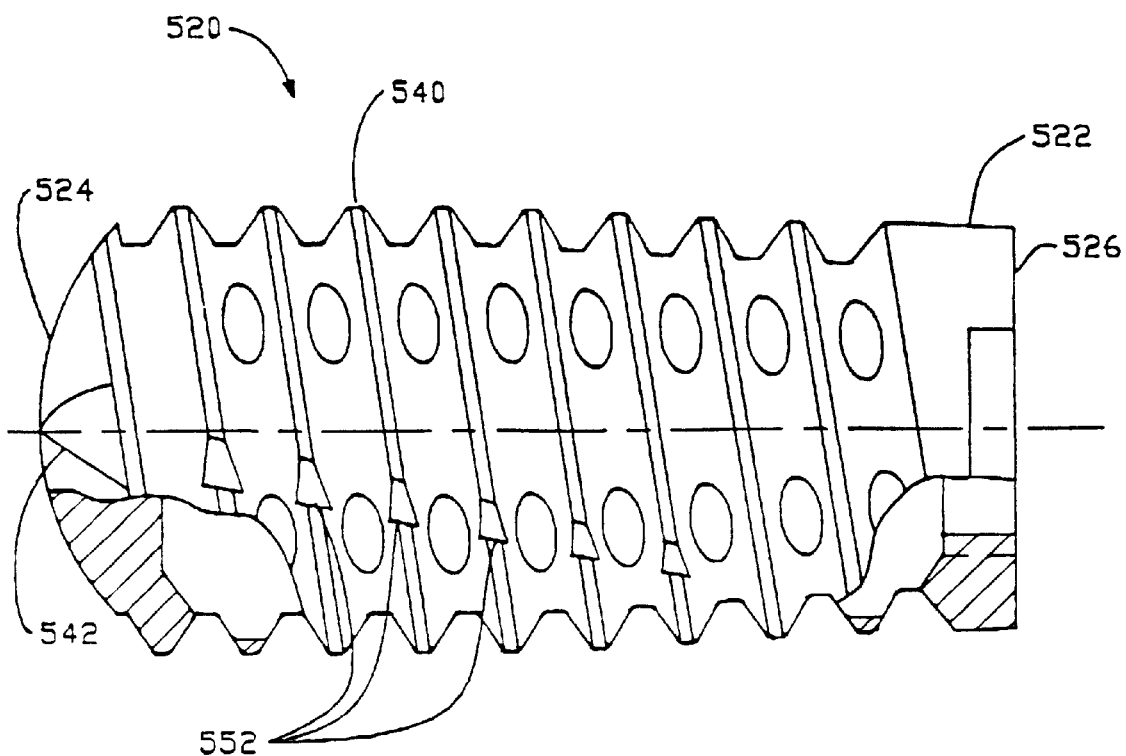
FIG.—24
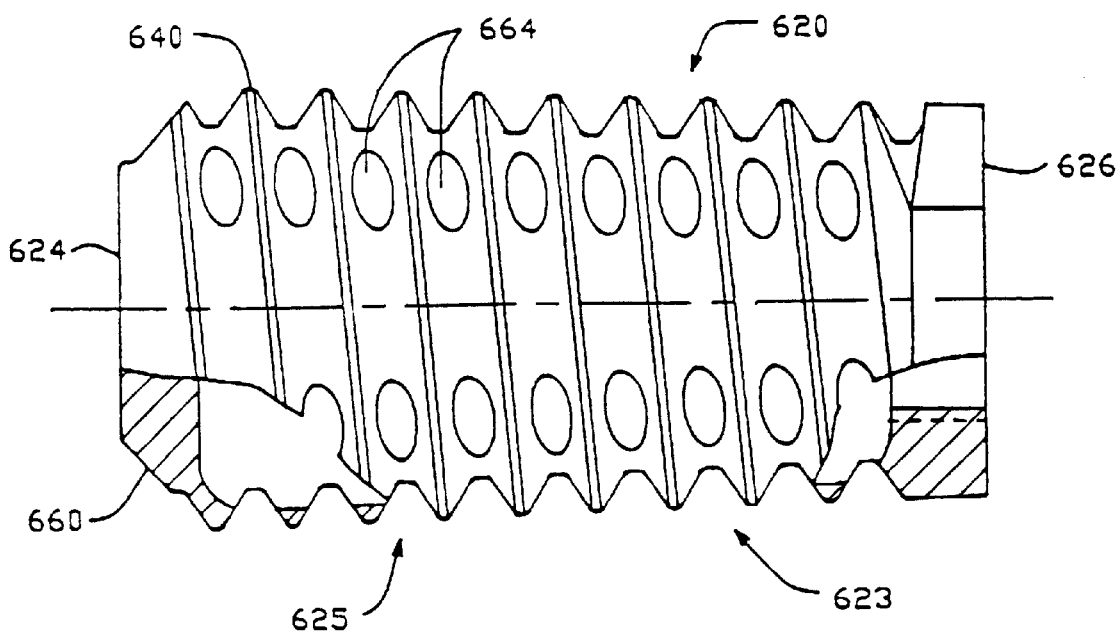
FIG.—25

CONICALLY SHAPED ANTERIOR FUSION CAGE AND METHOD OF IMPLANTATION

CROSS-REFERENCE

This is a continuation of appln. Ser. No. 08/354,364 filed on Dec. 12, 1994, now abandoned, which is a continuation-in-part of U.S. patent application Ser. No. 08/306,879, filed on Sep. 15, 1994 now abandoned.

BACKGROUND

1. Field of the Invention

The present invention is directed to devices and methods for facilitating the fusing of bone structures and more particularly the fusing together of adjacent vertebral bodies or bone structures.

2. Background of the Invention

Technical literature and patent documents disclose a number of devices and methods for fusing bones together. One such device which has proven to be successful is disclosed in U.S. Pat. No. 4,961,740, entitled "V-THREAD FUSION CAGE AND METHOD OF FUSING A BONE JOINT," which patent has been assigned the present assignee and which patent is incorporated herein by reference. The referenced patent discloses a fusion cage which is preferably cylindrical and has a thread formed as part of the external cylindrical surface. The fusion cage defines an internal cavity and apertures through the wall of the cage which communicate the external cylindrical surface with the internal cavity. The apertures are formed in the valleys of the thread. Normally two such cages are used to stabilized and fuse together adjacent vertebral bodies or bone structures.

In practice, using a posterior approach, a patient's vertebral bone structures are exposed and degenerate disk material located between the vertebral bone structures is removed. A threaded tap is used to tap a complementary thread in the upper and lower vertebral bone structures preparatory to the insertion of the above fusion cage. Once such tapping has been accomplished, using an introduction tool, the fusion cage is screwed into the space between the adjacent vertebral bone structures. The thread bites into the bone of the upper and lower vertebral bone structures, stabilizing the bone structures, and preventing the fusion cage from working out of this position due to patient movement. Generally two such fusion cages are applied using this technique. Once the two implants have been positioned, then bone growth inducing substances, such as bone chips, are packed into the internal cavity of the fusion cages. These bone growth inducing substances come into immediate contact with the bone from the vertebral bone structures which project into the internal cavity through the apertures. Such projection of bone is due to the fact that the apertures are formed in the valleys of the external thread of the fusion cage. Such immediate bone to bone contact between the vertebral bone structures and the bone pack within the fusion cages results in more rapid propagation of bone cells between the adjacent vertebral bone structures and thus a more rapid fusion of the adjacent vertebral bone structures.

It is to be understood that in the above method, bone growth inducing substances can be prepacked into the cages before the cages are implanted between the vertebral body structures.

SUMMARY OF THE INVENTION

The present invention is directed to a fusion cage which has been designed to be implanted using principally a posterior approach to the vertebral bone structures.

In a first embodiment of the present invention, the fusion cage includes a cage body having a proximal end and a distal end, said distal end having a diameter which is larger than the diameter of the proximal end. The distal end further is rounded with for example a bull nose in order to facilitate the insertion of the cage body relative to one or more bone structures. The distal end could alternatively have a snub nose with or without a starter turn of a thread. The snub nose has a starter diameter that is smaller than the diameter of the distal end. The cage body is preferably conically-shaped. This shape is particularly advantageous due to the fact that the normal lordosis of the vertebral bone structures defines a wedged-shape space for a vertebral disk between, for example, lumbar vertebrae. Accordingly, the conically-shaped body cage can be sized and selected in order to maintain or enlarge upon the normal lordosis.

In a second embodiment of the present invention the cage body can include a cylindrically-shaped portion and a conically-shaped portion. The cylindrically-shaped portion is located adjacent to the distal end and the conically-shaped portion extends from the cylindrically-shaped portion and tapers toward the proximal end.

In a third embodiment of the present invention, a fusion cage includes a cage body having a proximal end and a distal end with the proximal end having a diameter which is smaller than the diameter of the distal end. The distal end has a flute formed therein. Additionally, the cage body has an outer surface and at least one flute formed in the outer surface. These flutes act as a relief much as the flute placed on self-tapping screws in order to facilitate the insertion of the fusion cage using a twisting motion between two vertebral bone structures.

In a fourth embodiment of the invention, a fusion cage includes a cage body having a proximal end and a distal end, the proximal end having a diameter which is smaller than the diameter of the distal end. The cage body has an outer surface and a thread formed as part of the outer surface. The thread aids the cage body in being inserted. As the cage is inserted, it gradually spreads apart the vertebral bone structures in order to regain or enlarge the natural lordosis of the adjacent vertebral bone structures. As with other embodiments of the present invention, flutes can be provided in the thread in order to allow for enhanced thread tapping by the cage and for a smoother insertion of the fusion cage between the vertebral bone structures. Preferably two or three flutes would be formed spaced about the fusion cage in order that one flute would be engaging with or adjacent to an upper vertebral bone structures with another flute being engaging with or adjacent to a lower vertebral bone structure. Such a relationship maintains alignment of the fusion cage and prevent wandering as the fusion cage is introduced between the two vertebral bone structures. Without two or more flutes, wandering might occur due to the fact that the thread is only substantially engaged with the vertebral bone structures and not with the disk material between the vertebral bone structures, which disk material does not provide support to the thread.

In a further aspect of the invention, any of the above embodiments can be provided with a plurality of apertures through the fusion cage and an internal cavity with the apertures communicating between the internal cavity and the external surface of the fusion cage. Bone growth inducing substances, such as bone chips, can be packed into the internal cavity either before the fusion cage is inserted or after the fusion cage has reached a final insertion position, or packed in both before and after. The bone chips come in contact with the vertebral bone structures through the apertures in order to facilitate fusion between the adjacent vertebral bone structures.

In another aspect of the invention which can be included in any of the above embodiments, the cage body can have a round or bull nose distal end with one or more flutes formed in the round or bull nose distal end in order to enhance the self-tapping nature of the fusion cage and to prevent the cage from wandering.

In yet another aspect of the invention, introduction tools allow the fusion cage to be accurately positioned between the vertebral bone structures. A preferred introduction tool allows for the cage to be implanted and thereafter allows an end cap of the cage to be conveniently removed, if desired, in order to place bone growth inducing substances in the cage.

The method of the present invention affords access to adjacent vertebral bone structures using an posterior approach and procedure. Such posterior approach and procedure can be performed percutaneously using a minimally invasive technique with an introduction set including cannulas. Such a procedure is minimally invasive as the tissues can be spread using a set of cannula of increasing size and a small opening thereby developed through which a fusion cage can be inserted. Such a procedure is less traumatic to the tissue than an alternate posterior approach and procedure, also known as an posterior lumbar interbody fusion, where an incision is made, through the tissues. It is to be understood however that either posterior approach and procedure can be used with the fusion cage and fall within the scope of the invention.

After such access, using preferably a minimally invasive technique, degenerate disk material can be removed and, using a cannula and insertion tool, an appropriately shaped fusion cage can be screwed into place between the vertebral bone structures in order to stabilize the vertebral bone structures and allow for fusion. Either preparatory to insertion of the fusion cage or after it has been inserted, bone chips or other bone growth inducing substances can be inserted into the fusion cage to promote bone to bone contact and subsequent fusion.

It is to be understood that although the above-embodiments have been described with respect to the fusion of adjacent vertebral bodies or bone structures, that the present invention can be used (1) to fuse together a variety of bone structures, in addition (2) to being fused to one bone structure and used as, for example, a base for an implant or (3) to being used to reunite the pieces of a broken bone.

Other objects and advantages of the invention can be obtained through a review of the specification and the figures.

BRIEF DESCRIPTION OF THE FIGURES

Anterior Fusion Cage:

FIG. 6 depicts an alternative embodiment of the introduction tool.

FIGS. 7, 8, and 9 depict progressive stages in the method of inserting the anterior fusion cage between adjacent vertebral bone structures.

FIG. 12 depicts the right end (proximal end) view of the fusion cage of FIG. 10.

FIG. 13 depicts a side view of yet another embodiment of the anterior fusion cage of the present invention.

FIG. 14 depicts a left distal end (distal end) view of the fusion cage of the invention of FIG. 13.

FIG. 15 depicts a right end (proximal end) view of the fusion cage of the invention of FIG. 13.

FIG. 16 depicts a sectional view taken through line 16—16 of FIG. 13.

Posterior Fusion Cage:

FIG. 17 is a partially sectional side view of an embodiment of the posterior fusion cage of the invention.

FIG. 18 depicts a left end (distal end) view of the fusion cage of FIG. 17.

FIG. 19 depicts a right end (proximal end) view of the fusion cage of FIG. 17.

FIG. 20 depicts a view through line 20—20 of the fusion cage of FIG. 17.

FIGS. 21, 22, and 23 depict progressive stages in the method of inserting the posterior fusion cage between adjacent vertebral bone structures using the cage depicted in FIG. 25.

FIG. 24 depicts a side view of an alternative embodiment of the posterior fusion cage of the invention.

FIG. 25 depicts a side view of another embodiment of the posterior fusion cage of the invention.

Figure 26:
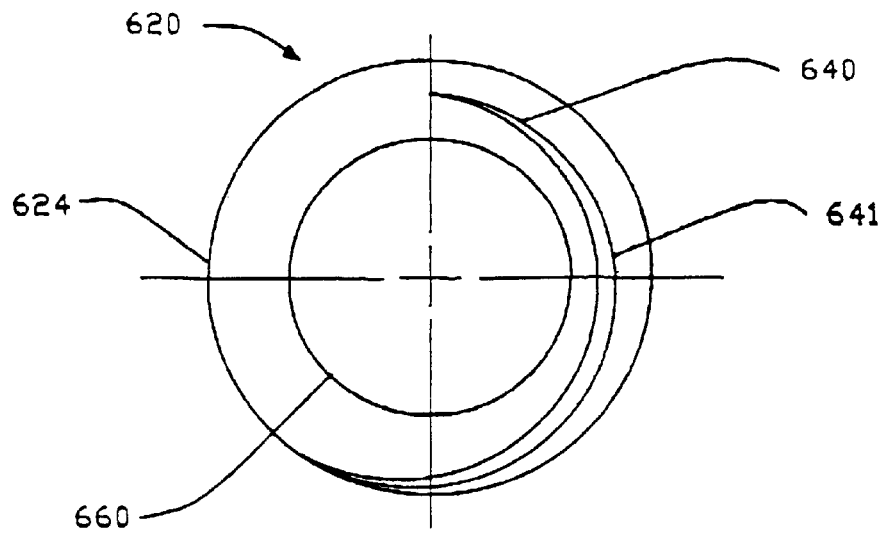

FIG. 26 depicts a left end (distal end) view of the embodiment of the fusion cage of FIG. 25.

Figure 1:
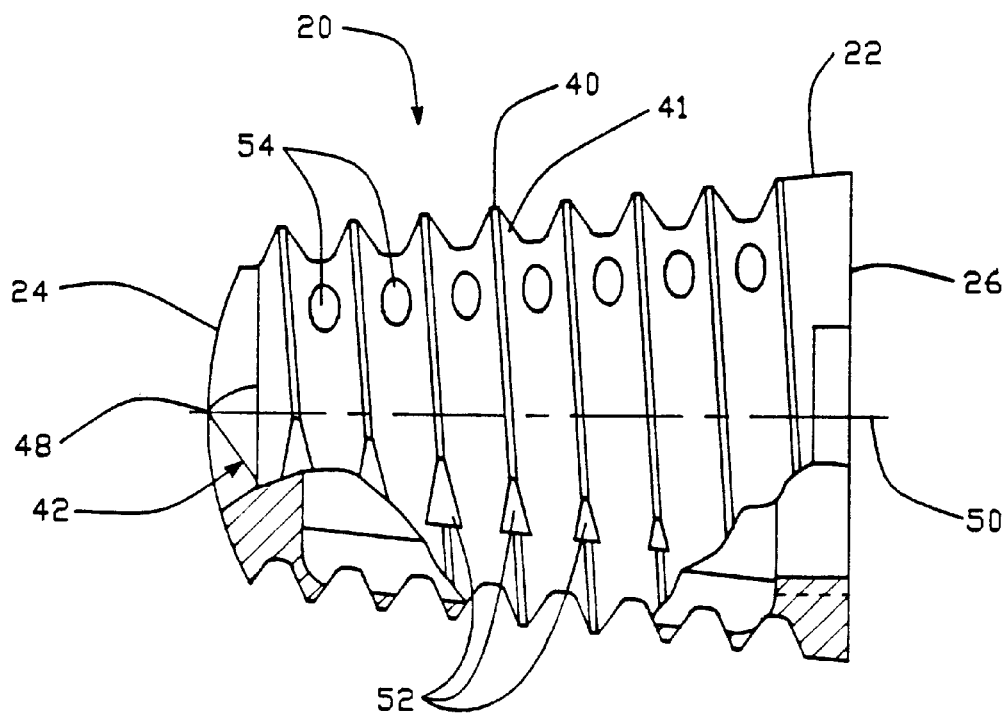
FIG. 1 is a partially sectional side view of an embodiment of the anterior fusion cage of the invention.
Figure 10:
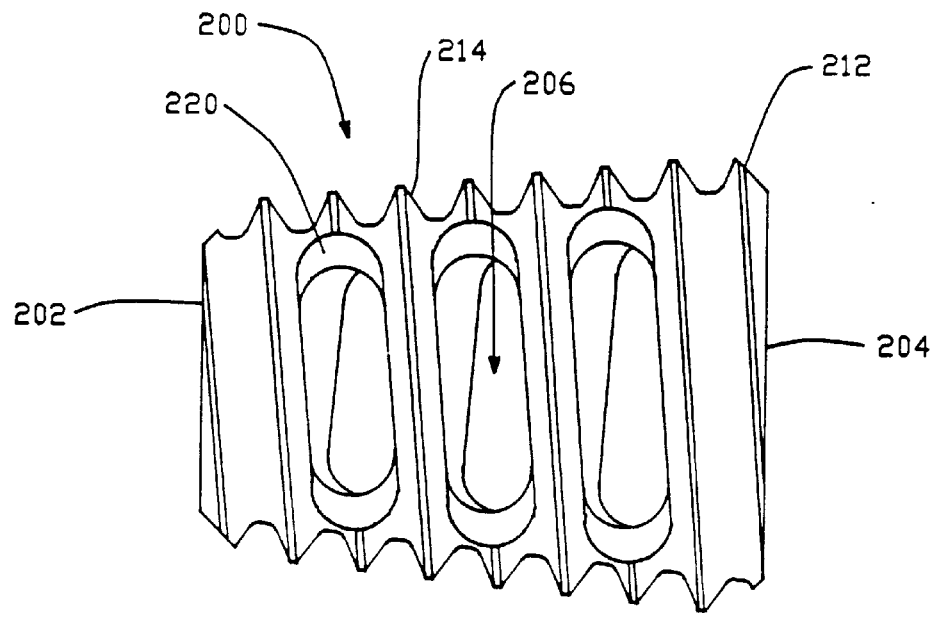
FIG. 10 depicts a side view of an alternative embodiment of the anterior fusion cage of the invention.
Figure 27:
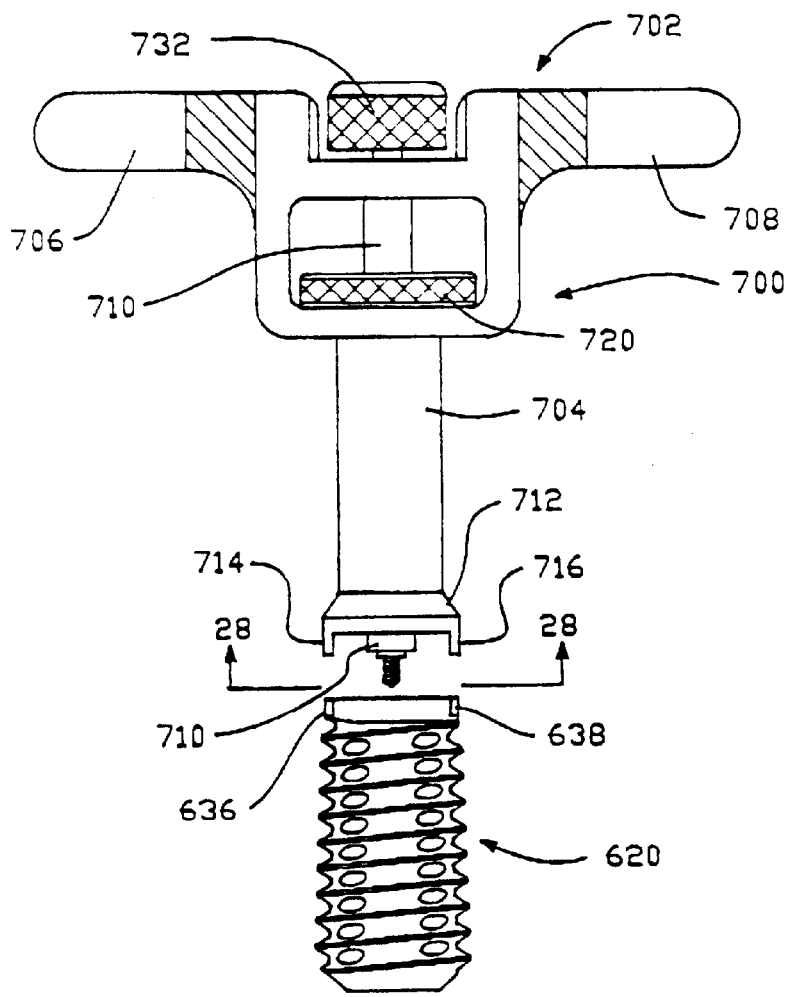

FIG. 27 depicts the fusion cage of FIG. 25 in conjunction with a new preferred insertion tool that can preferably be used with the anterior fusion cages of FIG. 1, 10 and 13, and with the posterior fusion cages of FIG. 17 and 25.

Figure 28:
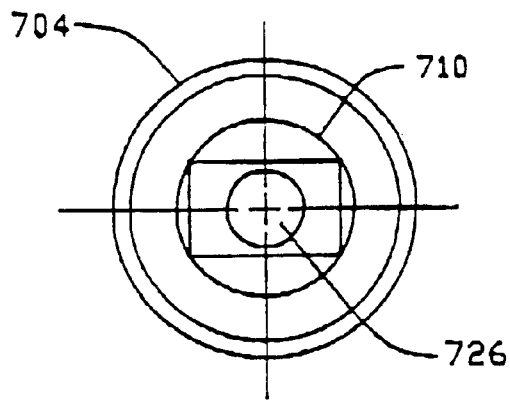

FIG. 28 depicts an end view of the insertion tool of FIG. 27 along line 28—28.

Figure 29:
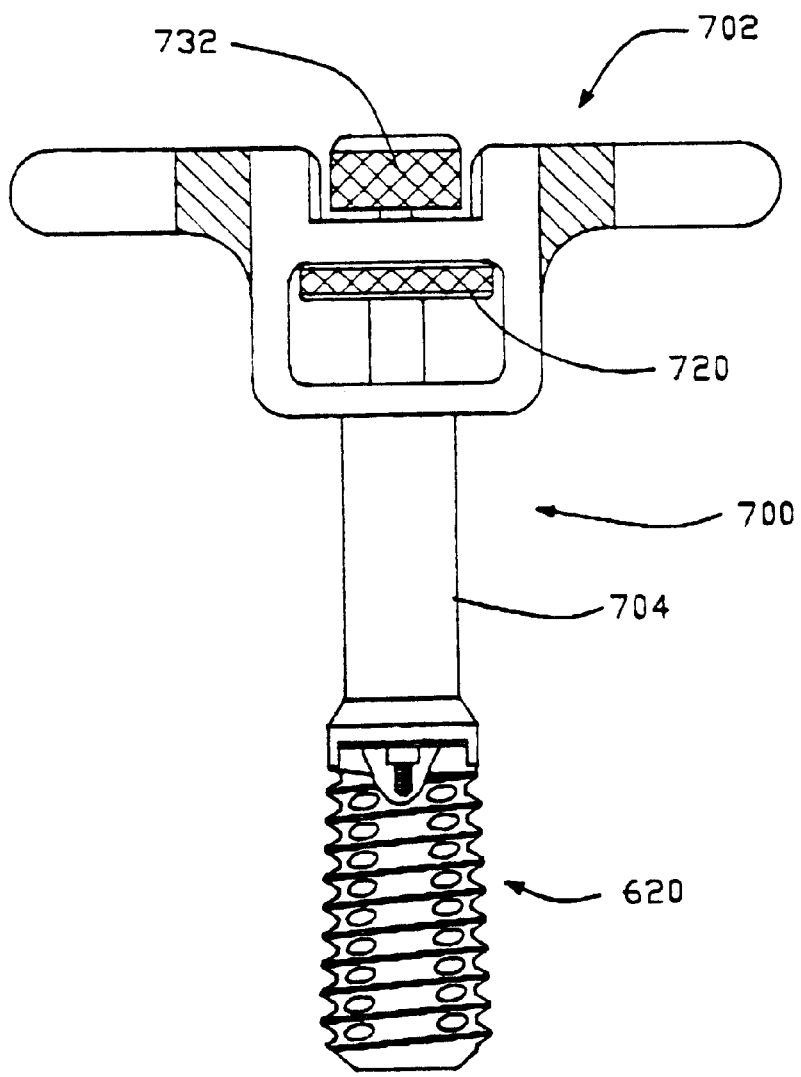

FIG. 29 depicts a partially broken away view of the fusion cage and the insertion tool of FIG. 27 connected together.

Figure 30:
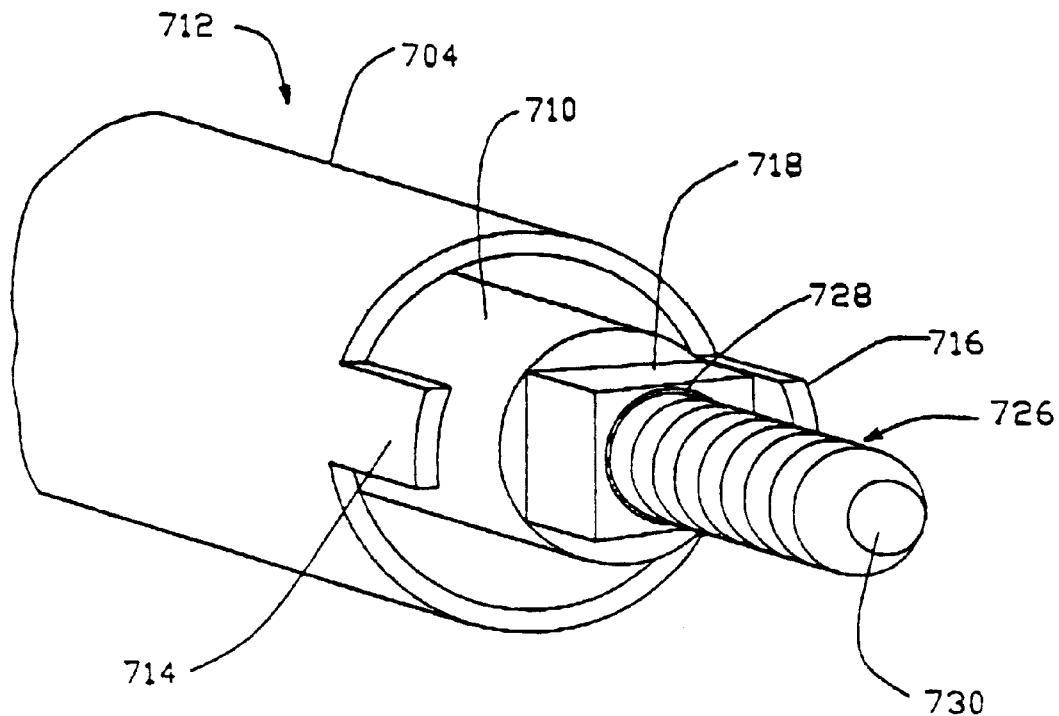

FIG. 30 depicts a perspective view of the end of the insertion tool depicted in FIG. 28.

Figure 31:
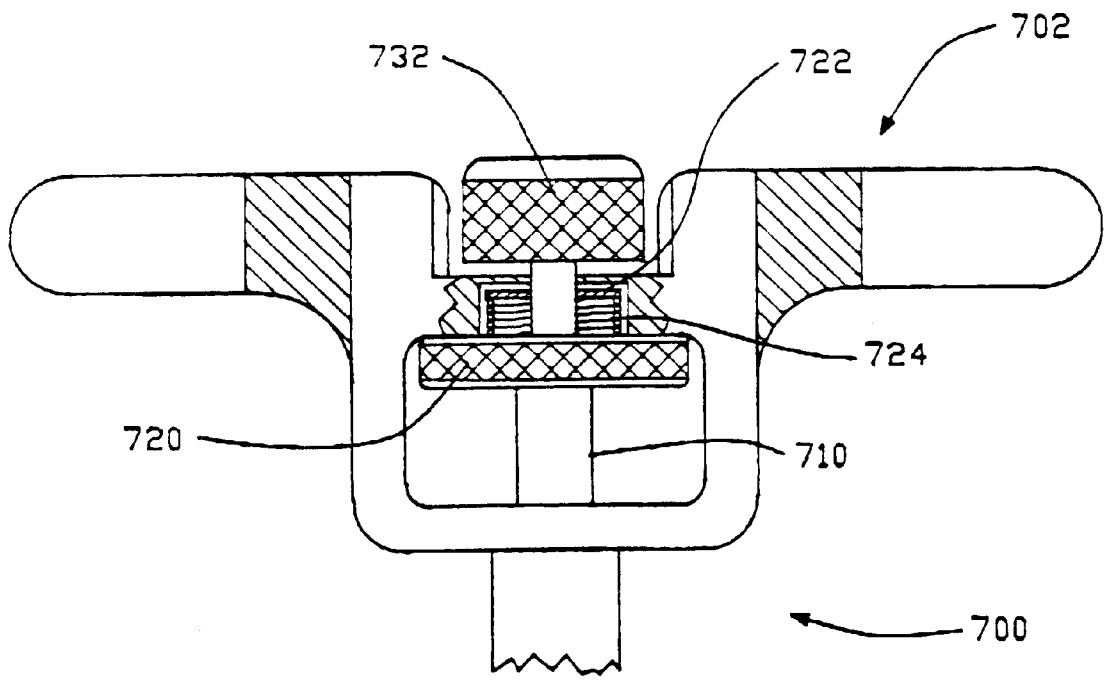

FIG. 31 depicts a partially sectional view of the handle of the insertion tool of FIG. 27.

DETAILED DESCRIPTION OF THE PREFERRED EMBODIMENT

Figure 5:
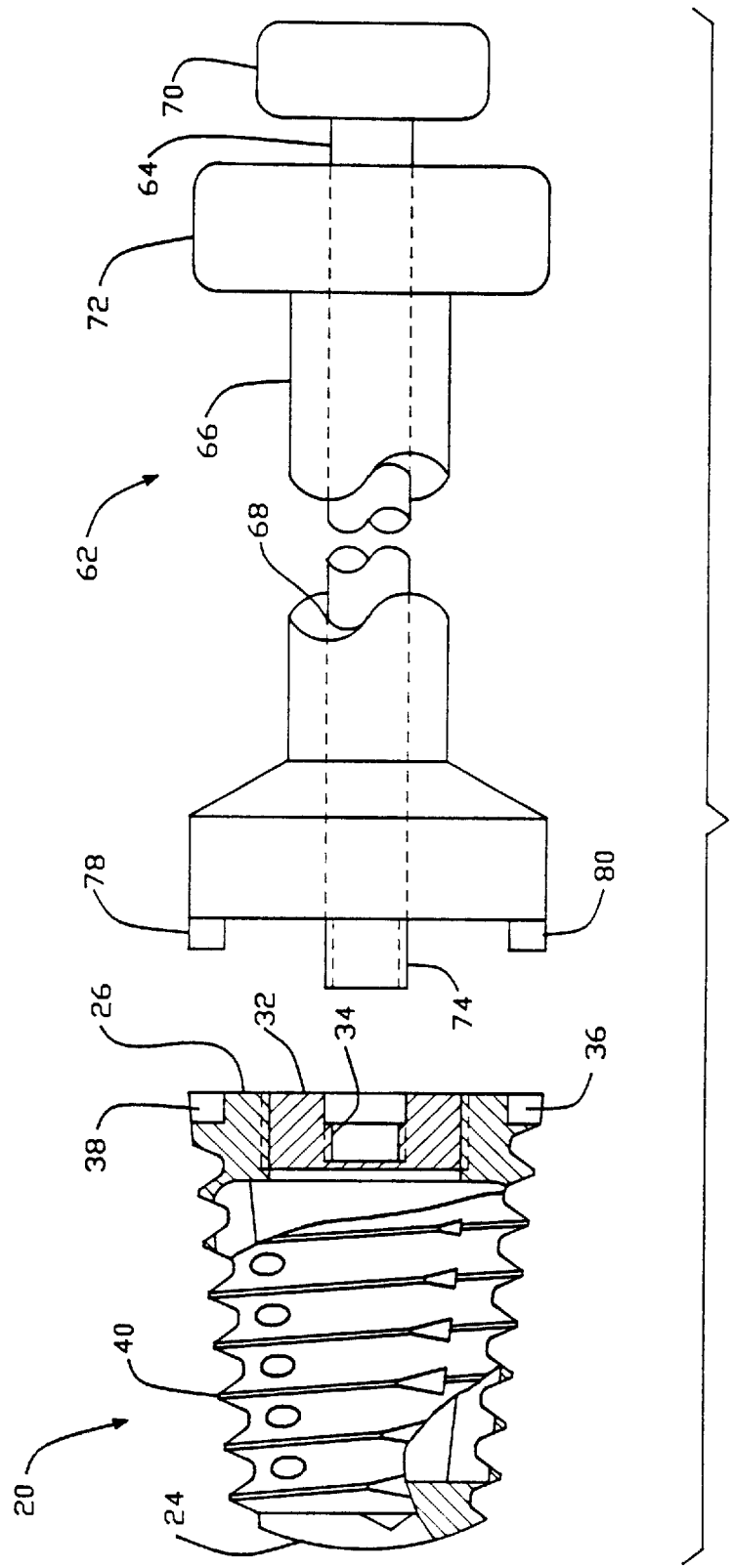
FIG. 5 depicts the fusion cage of FIG. 1 in conjunction with an introduction tool.

Anterior Fusion Cage:

With respect to the figures in a particular FIG. 1, a side view of the preferred embodiment of the fusion cage 20 is depicted. Fusion cage 20 includes a fusion cage body 22 which in this preferred embodiment is provided in the shape of a cone. Fusion cage 20 includes a distal end 24 and a proximal end 26. The distal end 24 in a preferred embodiment is rounded or bull nosed in order to facilitate the insertion of the fusion cage 20 relative to one or more bone structures. The proximal end 26 includes an opening 28 which communicates with an internal cavity 30 defined by the fusion cage 20. The opening 28 in a preferred embodiment is threaded so that it can receive an end cap or plug 32 (FIG. 5). End cap 32 is used to close off the proximal end 26 and retain bone growth inducing substances packed therein as described herein-below. As can be seen in FIG. 5, end cap 32 includes a threaded bore 34 which is designed to receive an insertion tool. The threaded bore 34 has an initial unthreaded, square or hex-shaped section 35 which can be used with a socket wrench to tightly position end cap 32 in opening 28 and which can be engaged by a preferred insertion tool of FIG. 27. Further the unthreaded portion of bore 34 could equally be cylindrical with an irregularity to allow for mating with an insertion tool, as well as having a variety of other shapes. The proximal end 26 further define first and second peripheral indentations 36, 38. These peripheral indentations 36, 38 receive tangs from an insertion tool as described hereinbelow for facilitating the insertion of the fusion cage 20.

A thread 40 is defined as part of the outer cylindrical surface 41 of the body 22. It is to be understood that the thread can be replaced with a plurality of discrete threads or a plurality of projections, ridges, protrusions, barbs, or spurs and be within the spirit and scope of the invention.

Figure 2:
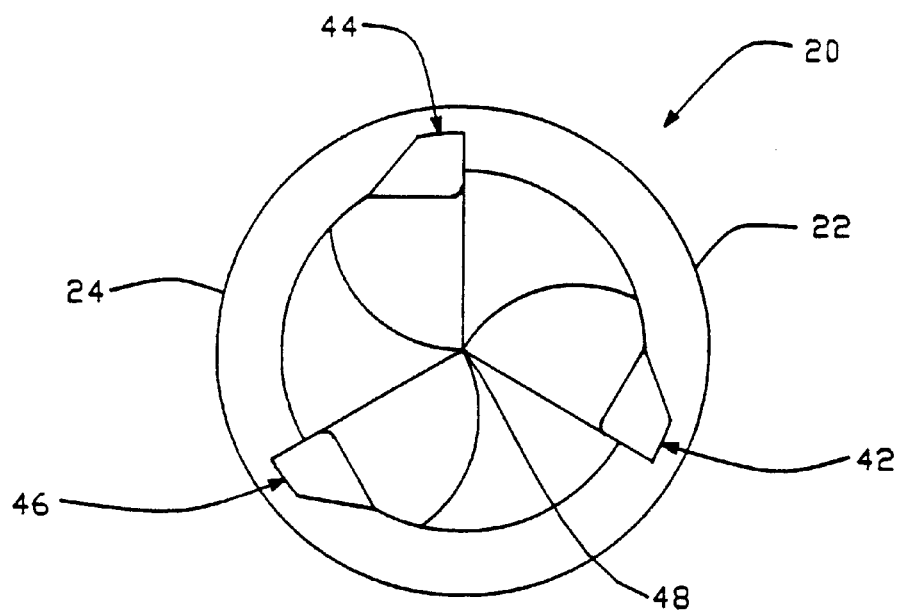
FIG. 2 depicts a left end (distal end) view of the fusion cage of FIG. 1.
Figure 3:
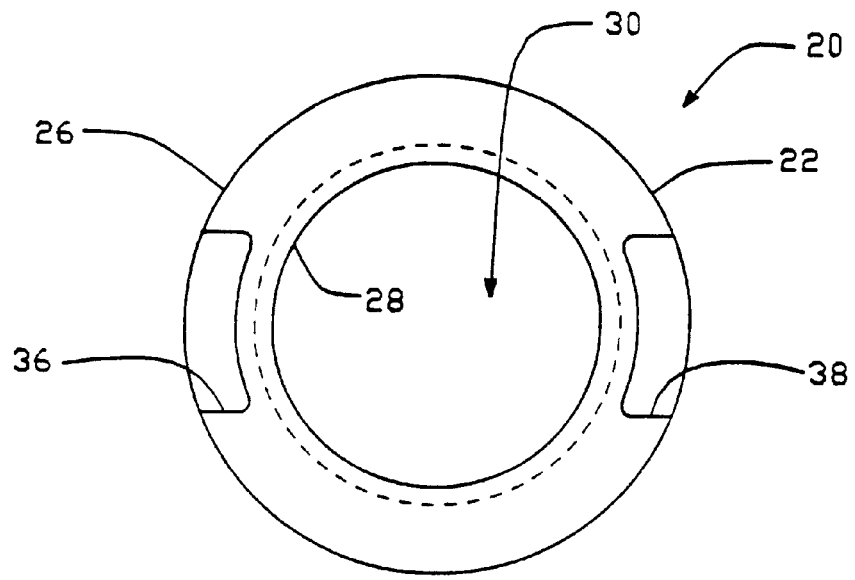
FIG. 3 depicts a right end (proximal end) view of the fusion cage of FIG. 1.

The rounded distal end 24, and at least some of the turns of thread 40 defined flutes or relief grooves 42, 44, and 46. (FIGS. 1, 2.) In a preferred embodiment, flutes 42, 44, and 46 meet at a central point 48 of the distal end 24 on the longitudal axis 50 of the fusion cage 20. In other embodiments the flutes can be smaller and not extend all the way to the central point 48 on the longitude axis 50. Still in other embodiments, the flutes can be eliminated from the distal end 24 and such embodiments are still within the spirit and scope of the invention.

The flutes extend from the distal end 24 toward the proximal end 26 as shown in FIG. 1 with respect to flute 42. These flutes are defined by the sections 52 which are removed from the thread. In a preferred embodiment, the flutes become narrower as they approach the proximal end 26 due to the fact that thread relief for purposes of self-tapping becomes less important as the cage reaches a final resting position. As shown in other embodiments, the flutes can be deeper and extend from the distal end completely to the proximal end. Still further in other embodiments the flutes can be confined to the first several turns of the thread adjacent to the distal end and/or to just the distal end.

Figure 4:
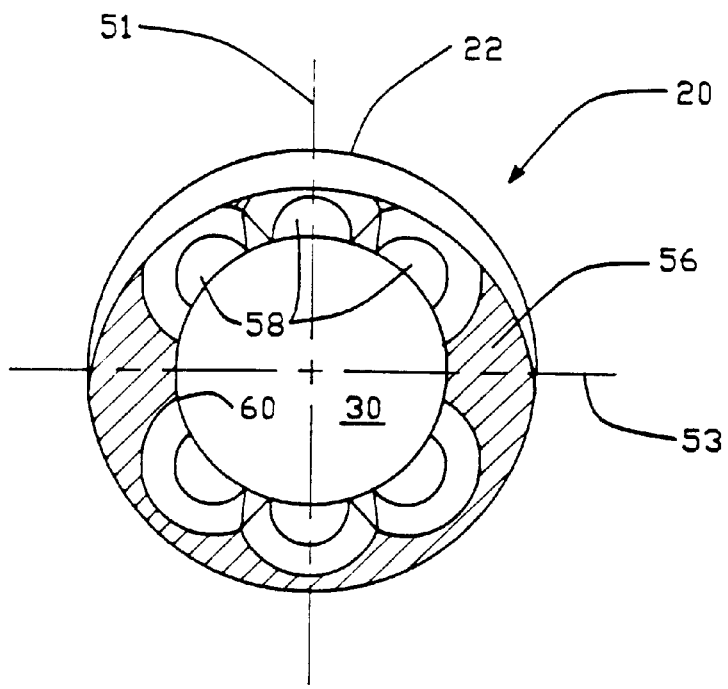
FIG. 4 depicts a view through line 4—4 of the fusion cage of FIG. 1.

As can be seen in FIGS. 1, 4, a plurality of apertures 54 are provided through wall 56 of the fusion cage 20. In a preferred embodiment, these apertures 54 are formed by broaching grooves 58 in the internal surface 60 of the internal cavity 30. The effect of such broaching is to remove material from the valleys between the turns of the thread 40, thus defining the aperture 54. The advantages of such an arrangement are taught by the above-referenced U.S. Pat. No. 4,961,740, which patent is incorporated herein by reference and allows for immediate bone to bone contact between the vertebral bodies or bone structures and the bone packed within the internal cavity 30 of the fusion cage 20.

The apertures 54 in a preferred embodiment increase in size from smaller apertures closer to the distal end 24 to a larger aperture closer to the proximal end 26. This increase in size allows for more bone to bone contact. Alternatively in the embodiment as shown in FIG. 1, all the apertures are of the same size.

As can be seen in FIG. 4, the apertures are clustered about a transverse axis 51, both at the upper and lower end of the axis. This is so that in position, the apertures come into contact with the upper and lower vertebral bone structures (FIG. 9) to encourage bone growth through the fusion cage from the vertebral bone structures. The lateral section of the fusion cage found along the other transverse access 53 do not have apertures in order to prevent growth of disk material which might interfere with the bone fusing process.

A preferred embodiment of the conically-shaped fusion cage 20 includes a fusion cage which is 23 millimeters in length having a distal end 24 with a diameter of 14 millimeters and a proximal end 26 with a diameter of 18 millimeters. The cage body is a right circular cone. The thread has a pitch of 30° and there are ten turns per inch with a thread depth of 0.053 inches. Further the cage is made of a titanium metal or alloy such as Ti64. Preferably this and the other disclosed fusion cages disclosed are machined. However, the processes such as molding, casting, or sintering can be used to accomplished formation of the fusion cages.

The cage is inserted between vertebral bodies using an insertion tool 62 (FIG. 5). Insertion tool 62 includes an inner handle 64 and an outer handle 66. The outer handle includes a bore 68 for receiving the inner handle 64. Handles 64, 66 include knobs 70, 72 respectively. The distal end of inner handle 64 defines a threaded shaft 74, having a reverse thread to facilitate easy removal, and the distal end of handle 66 define a cylindrical disk 76 which has first and second tangs 78, 80, projecting from the peripheral edge of the cylindrical disk 76. These tangs 78, 80 are designed to mate with the peripheral indentation 36, 38 of the fusion cage 20. For purposes of inserting the fusion cage between the vertebral bodies, the end cap 32 is inserted into the fusion cage 20 as shown in FIG. 5. Then the threaded shaft 74 of the inner handle is introduced into the threaded bore 34 of the end cap 32. After this is accomplished, the outer handle 66 is slid over the inner handle 64 and the tangs 78, 80 are positioned into engagement with the indentations 36, 38. In this arrangement, the fusion cage 20 can be anteriorly inserted into the space between the vertebral body structure using the insertion tool 62.

An alternative embodiment of the insertion tool is shown in FIG. 6. In this figure, insertion tool 82 includes a handle 84 with a knob 86. At the end of the insertion tool 82 distal from the knob 86 is a cylindrical disk 88 which has first and second tangs 90, 92, which have the same function as the above tangs 78, 80. Extending from the center of the cylindrical disk 88 along the centerline of the insertion tool 82 is a shaft 94 which has a ball detent 96. For use with insertion tool 82, the threaded bore 34 of the end cap 32 would be replaced with a bore having a lip which could engage with the ball detent 96 of the insertion tool 82.

It is to be understood that the insertion tool depicted in FIG. 27 and described below is preferable to the above described insertion tools for both the anterior fusion cages and the below described posterior fusion cages.

The method for inserting the fusion cage 20 of FIG. 1 using an anterior approach and procedure to the vertebral bodies is as follows. It is to be understood that although the focus of this discussion is on a laparoscopic procedure, that the anterior approach and procedure can also include a more invasive procedure where a long incision is made in the abdomen wall.

With an anterior approach, using an introduction set such as described by way of example only, in U.S. Pat. No. 4,863,430, entitled "INTRODUCTION SET WITH FLEXIBLE TROCAR WITH CURVED CANNULA," which is incorporated by reference, but however with larger diameter instruments, an amount of disk material is removed between the two vertebral bodies or bone structures which are to be fused together. This procedure is accomplished through a cannula position adjacent to the vertebral bone structures. With the same or a larger diameter cannula, the fusion cage 20 can be introduced adjacent to the vertebral bone structures. In a first procedure, the fusion cage is packed with bone growth substances and the end cap 32 is affixed to the fusion cage 20. Insertion tool 62 is then secured to the fusion cage 20 and the fusion cage is guided through the cannula to a location adjacent to the upper and lower vertebral body such as presented schematically in FIGS. 7, 8, 9, by upper body 98 and lower body 100. In the initial position as shown in FIG. 7, the fusion cage 20 is adjacent to the anterior surfaces 102, 104 of the vertebral bodies 98, 100. As the introduction tool is turned, the thread 40 of the fusion cage 20 bites into the vertebral bodies 98, 100. Further turning of the introduction tool causes the fusion cage to move through the position shown in FIG. 8 to the final resting position shown in FIG. 9, where the distal end 24 is moved adjacent to the posterior sections 106, 108 of the vertebral bone structures 98, 100. As this occurs, the fusion cage 20 increases the lordosis or spacing between the vertebral bodies, basically distracting the vertebral bodies and causing the vertebral bodies to pivot about the posterior sections 106, 108, with such posterior sections acting like a hinge. It is noted that most of the distraction occurs adjacent to the anterior sections, but that distractions also occur at the posterior sections where the hinged effect is exhibited. Preferably, the lordosis is increased over the normal lordosis in order to stabilize the vertebral bone structures prior to fusion occurring. Stabilization occurs due to the fact that increased lordosis places additional stress on the anterior longitudinal ligaments which are part of the anatomy holding the vertebral bodies in place.

Once the fusion cage 20 is appropriately positioned, the handle 64 of the insertion tool 62 is unscrewed from the cap 32 and the fusion handle 62 is pulled away from the fusion cage.

Figure 11:
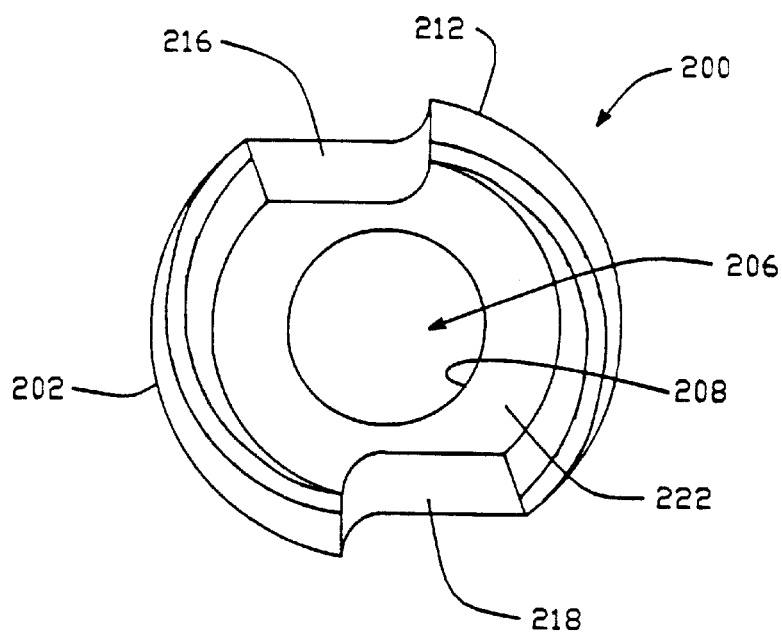
FIG. 11 depicts the left end (distal end) view of the fusion cage of FIG. 10.

An alternative embodiment of a fusion cage 200 is shown in FIGS. 10, 11, and 12. Fusion cage 200 includes a distal end 202 and an a proximal end 204. Fusion cage 200 includes an internal cavity 206. End caps not shown can be used to close the ports 208, 210 of distal and proximal ends 202, 204. A thread 212 is defined on the external conical surface 214 of the fusion cage 200. Defined by the thread 212 are first and second flutes 216, 218, which in this embodiment extend from the distal end 202 to the proximal end 204. These flutes provide thread relief allowing the fusion cage 200 to be self-tapping.

The fusion cage 200 includes a plurality of elongated apertures 220 which are formed through the side walls of a fusion cage 200. The elongated apertures 202 are formed in such a way that the internal conical surface 214 is spaced away from the internal surface 224 of the internal cavity 206 by the thickness of the sidewall 222.

A further embodiment of the invention is shown in FIGS. 13, 14, 15 and 16. In FIG. 16 the fusion cage 300 has distal and proximal ends 302 and 304 respectively. The fusion cage 300 defines an internal cavity 306, and ports 308 and 310 defined through the distal and proximal ends 302 and 304 respectfully. A thread 312 is defined as part of the external conical surface 314 of the fusion cage 200. First, second and third flutes 316, 318, and 320, are defined in the thread 312 from the distal end 302 to the proximal end 304. These flutes give the fusion cage 300 an enhanced self-tapping advantage. These flutes are equally spaced about the fusion cage 300 in a manner similar to the flutes of the fusion cage embodiment 20 in FIG. 1.

A plurality of aperture 322 is provided through the external conical surface 314 of the fusion cage 300 and through the side wall 324 opening into the internal cavity 306. Accordingly, at the location of the aperture 322 the external surface 314 is held away from the internal surface 326 by the thickness of the side wall 324.

Posterior Fusion Cage:

With respect to the figures in a particular FIG. 17, a side view of the preferred embodiment of the posterior fusion cage 420 is depicted. Fusion cage 420 includes a fusion cage body 422 which in this preferred embodiment is provided with a conically-shaped portion 423 and a cylindrically-shaped portion 425. It is to be understood that alternatively the entire body 422 can be conically-shaped. Further, as appropriate the shape of the cage body 422 can be more complex with various conical and/or cylindrical configurations. Fusion cage 420 includes a distal end 424 and a proximal end 426. The distal end 424 in a preferred embodiment is rounded or bull nosed in order to facilitate the insertion of the fusion cage 420 relative to one or more bone structures. The proximal end 426 includes an opening 428 (FIG. 19) which communicates with an internal cavity 430 (FIG. 20) defined by the fusion cage 420. The opening 428 in a preferred embodiment is threaded so that it can receive an end cap or plug such as 32 of the embodiment in FIG. 5. End cap is used to close off the proximal end 426 and retain bone growth inducing substances, such as bone chips, packed therein as described herein-below. As can be seen in the embodiment of FIG. 5, end cap 32 includes a threaded bore 34 which is designed to receive an insertion tool. The threaded bore 34 has an initial unthreaded, square or hex-shaped portion 35 which can be used with a socket wrench to tightly position end cap 32 in opening 428 and which can also be engaged by the insertion tool of FIG. 27 described below. Portion 35 can be otherwise shaped as described above.

The proximal end 426 of the embodiment of FIG. 19 further define first and second peripheral indentations 436, 438 which are centered about transverse axis 453. These peripheral indentations 436, 438 receive tangs from an insertion tool as described below for facilitating the insertion of the fusion cage 420. These identifications are also used to line up the cage 420 for proper insertion between the vertebral bodies as discussed below.

A thread 440 is defined as part of the outer cylindrical surface 441 of the body 422. It is to be understood that the thread can be replaced with a plurality of interrupted or discrete threads or a plurality of projections, ridges, protrusions, barbs, or spurs and be within the spirit and scope of the invention.

The rounded distal end 424, and at least some of the turns of thread 440 can in a preferred embodiment can define flutes or relief grooves 442, 444, and 446 (FIGS. 24, 25). It is to be understood that in alternative embodiments the flutes can be eliminated from the distal end 424 and the thread 440, since for example, the bore for the insertion of the fusion cage 420 between the vertebral bodies can be pre-tapped. Still in alternative embodiment, the flutes on the distal end can remain to assist in the insertion of the cage 420 between the vertebral bodies. In a preferred embodiment, flutes 442, 444, and 446 meet at a central point 448 of the distal end 424 on the longitudal axis 450 of the fusion cage 420. In other embodiments the flutes can be smaller and not extend all the way to the central point 448 on the longitude axis 450. Still as indicated above in other embodiments, the flutes can be eliminated from the distal end 424 and the thread 440 and such embodiments are still within the spirit and scope of the invention.

The flutes can extend from the distal end 424 toward the proximal end 426 as shown in the alternative embodiment in FIG. 24 with respect to flute 542. These flutes are defined by the sections 552 which are removed from the thread. In this embodiment, the flutes become narrower as they approach the proximal end 526 due to the fact that thread relief for purposes of self-tapping becomes less important as the cage reaches a final resting position. As shown in other embodiments, the flutes can be deeper and extend from the distal end completely to the proximal end. Still further in other embodiments the flutes can be confined to the first several turns of the thread adjacent to the distal end and/or to just the distal end.

With respect to FIGS. 17, 20, a plurality of apertures 454 are provided through wall 456 of the fusion cage 420. In a preferred embodiment, these apertures 454 are formed by broaching grooves 458 in the internal surface 460 of the internal cavity 430. The effect of such broaching is to remove material from the valleys between the turns of the thread 440, thus defining the aperture 454. The advantages of such an arrangement are taught by the above-referenced U.S. Pat. No. 4,961,740, which patent is incorporated herein by reference and allows for immediate bone to bone contact between the vertebral bodies or bone structures and the bone packed within the internal cavity 430 of the fusion cage 420.

The apertures 454 in a preferred embodiment increase in size from smaller apertures closer to the proximal end 426 to a larger aperture closer to the distal end 424. This increase in size allows for more bone to bone contact. Alternatively in the embodiment as shown in FIG. 17, all the apertures are of the same size.

As can be seen in FIG. 20, the apertures are clustered about a transverse axis 451, both at the upper and lower end of the axis. This is so that in position, the apertures come into contact with the upper and lower vertebral bone structures (FIG. 23) to encourage bone growth through the fusion cage from the vertebral bone structures. The lateral sections of the fusion cage found along the other transverse axis 453 do not have apertures in order to prevent growth of disk material which might interfere with the bone fusing process. As can be seen viewing both FIGS. 19 and 20 together, the indentation 436 and 438 are centered on the axis 453 with the aperture 454 centered on axis 451. Axis 451 is preferably perpendicular to axis 453. The insertion tool has tangs that are inserted in indentation 436 and 438. Accordingly, the position of the insertion tool defines the position of the apertures 454 in that upon insertion the apertures 454 can be put in contact with the upper and lower vertebral bodies to allow bone ingrowth and prevent lateral ingrowth of disk material.

A preferred embodiment of the conically-shaped fusion cage 420 includes a fusion cage which is 28 millimeters in length having a distal end 424 with a diameter of 16 millimeters and a proximal end 426 with a diameter of 14 millimeters. The cage body is a right cylinder from the distal end 424 extending toward the proximal end 426 for four turns of thread 440. Then the cage 420 becomes a right cone from the remaining five turns of thread 440 until thread 440 terminates at proximal end 426. This conically-shaped portion is defined by relief 455 of 3.20°. The thread has a pitch of 30° and there are ten turns per inch with a thread depth of 0.053 inches. Further the cage is made of a titanium metal or alloy such as Ti64. Preferably this and the other disclosed fusion cages disclosed are machined. However, the processes such as molding, casting or sintering can be used to accomplished formation of the fusion cages.

The cage is inserted between vertebral bodies using a preferred insertion tool 700 shown in FIG. 27. Insertion tool 700 includes a handle 702 with an outer shaft 704 extending therefrom. The handle 702 includes first and second wings 706, 708 which make the handle easier to grab. The outer shank 704 is hollow and disposed within the outer shaft is an intermediate shaft 710 which can be seen extending from the cage engaging in 712 of the shaft 704. The cage engaging end 712 includes first and second tangs 714, 716 which can be inserted in the indentation of the cage such as for example indentations 436, 438, as shown in FIG. 19, and indentations 636 and 638 shown in FIG. 27. The end of shaft 710 includes a square-shaped drive 718 which engages the square-shaped unthreaded portion of the otherwise threaded bore such as bore 34 of an end cap such as end cap 32 as shown in FIG. 5. This same end cap can be used in the end of fusion cage 620. Alternatively, the square drive can be hexagonal shape with the unthreaded portion of the bore 34 being hexagonal shaped to provide the necessary mating arrangement. Other mating shapes can also be used. A first knurled knob 720 is secured to immediate shaft 710 in order to provide a mechanism for rotating intermediate shaft 710 inside of outer shank 704. As can be seen in FIG. 31, the intermediate shank 710 is spring biased relative to the handle 702 with a spring 722. Spring 722 is imbedded in a bore 724 of handle 702. In FIG. 31, the first knurled knob 720 and the shank 710 are pulled back and thus compress the spring 722. In FIG. 27, the first knurled knob 720 is released and the spring (not shown) is uncompressed.

An inner shaft 726 is located within a bore 728 of the intermediate shaft 710. The inner shaft 726 ends in a threaded portion 730 (FIG. 30). The other end of inner shaft 726 is secured to the second knurled knob 732. Inner shaft 726 is free to rotate, through the use of the second knurled knob 72, within the bore 728 of the intermediate shaft 710. In addition the inner shaft 728 has limited freedom of motion along the longitudinal axis of the inner shaft 726.

The operation of the insertion tool 700 is as follows. With the insertion tool 700 not secured to a fusion cage, the insertion tool is as depicted in FIG. 27 with the threaded portion 730 being either received entirely within bore 728 or extending a minimal amount out of bore 728. With the end cap secured in the fusion cage, the exposed square drive 718 is mated with the square portion of the bore in the end cap. The tangs 712, 714 are aligned with the indentations 636 and 638 and the tool is pushed in so that the tang 712, 714 are received in the indentations 636, 638. As this occurs, the knurled knob 730 moves up to the position as shown in FIG. 29 and 31, compressing the spring. After this occurs, the second knurled knob 732 can be turned clockwise in order to engage the threaded portion 730 of the inner shaft 726 with the threaded portion of the bore of the end cap. This draws the fusion cage securely to the insertion tool 700 as shown in FIG. 29. In this position, the cage is ready for insertion between the vertebral bodies. The handle 702 is then used to screw the cage between the vertebral bodies into the final resting position. Once the cage is in the final resting position, second knurled knob 732 is turned counter-clockwise in order to back the threaded 730 out of the threaded portion of the bore of the end cap. As this occurs, the spring 722 causes the square drive 718 to push against the end cap maintaining the end cap in its position relative to the fusion cage until the threaded portion 730 disengages itself from the threaded portion of the end cap, and the insertion tool 700 is disengaged from the fusion cage and can be removed. Thus the square drive, which is spring loaded, prevents the end cap on the cage from screwing out when the insertion tool is removed from the cage.

Should it be desired to move the end cap with the fusion cage in place, the square drive 718 can be inserted into the square portion of the threaded bore. The threaded portion 730 of the inner shaft 726 can then be screwed into engagement with the threaded portion of the threaded bore of the end cap, preferably with the tangs unaligned with the indentations. The first knurled knob 720 can then be turned in order to back the cap out of the fusion cage. A reverse of this operation can be used to insert the end cap into the fusion cage after additional bone growth inducing substances are packed into the fusion cage.

The method for inserting the fusion cage 420 of FIG. 17 using a posterior approach and procedure to the vertebral bodies is as follows. Both a minimally invasive procedure and a more invasive procedure where a long incision is made in the back can be used.

With a posterior approach, using an introduction set such as described by way of example only, in U.S. Pat. No. 4,863,430, entitled "INTRODUCTION SET WITH FLEXIBLE TROCAR WITH CURVED CANNULA," which is incorporated by reference, but however with larger diameter instruments, an amount of disk material is removed between the two vertebral bodies or bone structures which are to be fused together. This procedure is accomplished through a cannula position adjacent to the vertebral bone structures. Then if required a thread is tapped in the upper and lower vertebral bodies. With the same or a larger diameter cannula, the fusion cage 420, or alternatively the preferred fusion cage 620 of FIG. 25, can be introduced adjacent to the vertebral bone structures. In a first procedure, the fusion cage is packed with bone growth substances and the end cap is affixed to the fusion cage 620. Insertion tool 700 is then secured to the fusion cage 620 and the fusion cage is guided through the cannula to a location adjacent to the upper and lower vertebral body such as presented schematically in FIGS. 21, 22, 23, by upper body 498 and lower body 500. In the initial position as shown in FIG. 21, the fusion cage 620 is adjacent to the posterior sections 502, 504 of the vertebral bodies 498, 500. As the introduction tool is turned, the thread 640 (FIG. 25) of the fusion cage 620 bites into the vertebral bodies 498, 500. Further turning of the introduction tool causes the fusion cage to move through the position shown in FIG. 22 to the final resting position shown in FIG. 23, where the distal end 624 is moved adjacent to the anterior sections 506, 508 of the vertebral bone structures 498, 500. As this occurs, the fusion cage 620 increases the lordosis or spacing between the vertebral bodies, basically distracting the vertebral bodies. It is noted that most of the distraction occurs adjacent to the anterior sections, but that distraction also occur at the posterior sections. Preferably, the lordosis is increased over the normal lordosis in order to stabilize the vertebral bone structures prior to fusion occurring. Stabilization occurs due to the fact that increased lordosis places additional stress on the anterior longitudinal ligaments which are part of the anatomy holding the vertebral bodies in place.

Once the fusion cage 620 is appropriately positioned, the insertion tool 700 is unscrewed from the cap and the insertion tool 700 is pulled away from the fusion cage.

It is to be understood that the cage can be implanted without the use of a cannula by making a larger incision in the back. With this arrangement the bone chips would more often be packed into the cage after the cage reaches its final position and then an end cap would be secured t the cage. In the final position apertures 454 or 654 (embodiment of FIG. 25) would be positioned adjacent vertebral bodies 498 and 500. No matter which procedure is used to insert the cage 420 or 620, it is advantageous to provide a bore between the vertebral bodies that is less than the diameter of the distal end 424. Thus, for a cage 420 or a cage 620 with a distal end having an 18 diameter, the bore would be 14 millimeters. Inserting the cage 420 or the cage 620 would cause the vertebral bodies to be distracted (FIG. 22) and then rock back (FIG. 23) onto the conically-shaped portion of the fusion cage 420.

An alternative embodiment of a fusion cage 520 is shown in FIGS. 24. Fusion cage 520 includes a distal end 524 and an a proximal end 526. A thread 540 is defined on the external surface of the fusion cage 520. Defined by the thread 540 are flutes 542, 544, 546, which in this embodiment extend from the distal end 524 toward the proximal end 526. These flutes provide thread relief 552 allowing the fusion cage 520 to be self-tapping.

Still an alternative and preferred embodiment of the invention as mentioned above is shown in FIG. 25. In this embodiment the fusion cage 620 includes a blunt or flat distal end 624 and a proximal end 626. As in the other embodiments, the fusion cage is conically-shaped, and includes a thread 640 and aperture 654.

FIG. 26 includes a view of the distal end 624 of the fusion cage 620. This distal end 624 uses a snub nosed portion that is closed. The diameter of the snub nosed portion 660 is smaller than the largest root of the thread 640 at the distal end 624. As can be seen in FIG. 26, the thread 640 has a starter portion or starter turn 641 which includes approximately the first half turn of the thread 640. The diameter of the starter portion 641, as can be seen FIG. 26, is substantially less than the outside diameter of the four turns of thread 640 which comprised the cylindrical portion 625. From the cylindrical portion 625, the cage 620 and the thread 640 taper off to the proximal end 626 and define the conically-shaped portion 623.

The starter turn 641 of thread 640, as the name implies, assist in promoting the proper engagement of the thread 640 with the upper and lower vertebral bodies. In this embodiment, as in prior embodiments, the distal end has a diameter of approximately 16 millimeters. The diameter of the snub nosed portion 660 is about 10 millimeters.

Industrial Applicability

The present invention affords the advantages of a fusion cage which can be introduced through a posterior approach in order to maintain or increase lordosis between adjacent vertebral bodies. The fusion cage has the advantage of being conically-shaped and self-tapping through the use of external flutes. The flutes additionally assist in keeping the fusion cage aligned and centered as the cage is being inserted between the vertebral bone structures.

Other advantages, aspects, and objects of the invention can be obtained through a review of the claims and the appended figures.

It is to be understood that additional embodiments of the invention can be constructed and fall within the spirit and scope of the claims.

We claim:

1. A fusion cage for promoting fusion with one or more bone structures, which comprises:

a cage body having a proximal end and a distal end, and defining an internal cavity and a longitudinal axis, said proximal end having a diameter which is smaller than a diameter of said distal end, said cage body having an outer surface and a thread formed into said outer surface, and a plurality of radial apertures extending through said outer surface in communication with said internal cavity, said apertures increasing in size from said distal end toward said proximal end;

and said distal end being rounded to facilitate insertion relative to one or more bone structures.

2. An apparatus for promoting fusion with one or more bone structures, comprising an implant member having proximal and distal end portions and defining a longitudinal axis, the implant member including at least a longitudinal portion extending along at least a major portion of the length of the implant member, the longitudinal portion having an arcuate cross-sectional dimension transverse to the longitudinal axis and defining a generally tapered configuration whereby the cross-sectional dimension of the longitudinal portion gradually decreases from distal to proximal, the distal end portion defining an entry end surface, the entry end surface being closed to facilitate insertion relative to one or more bone structures.

3. The apparatus according to claim 2 wherein the entry end surface of the implant member is generally rounded.

4. The apparatus according to claim 2 wherein the longitudinal portion defines a frusto-conical configuration.

5. The apparatus according to claim 4 wherein the implant member includes an exterior surface portion having discontinuities to permit bone ingrowth.

6. The apparatus according to claim 5 wherein the external surface portion includes a threaded portion to facilitate positioning adjacent the one or more bony structures.

7. The apparatus according to claim 4 wherein the implant member includes a hollow interior cavity dimensioned to accommodate bone growth inducing substances.

8. The apparatus according to claim 2 wherein the implant member includes a second longitudinal portion, the second longitudinal portion defining a cylindrical configuration having a cross-sectional dimension which remains constant throughout the length of the second longitudinal portion.

9. An apparatus for promoting fusion with one or more bone structures, comprising an implant member having proximal and distal end portions and defining a longitudinal axis the implant member including at least a longitudinal portion extending along at least a major portion of the length of the implant member, the longitudinal portion having an arcuate cross-sectional dimension transverse to the longitudinal axis and defining a generally frusto-conical configuration whereby the cross-sectional dimension of the longitudinal portion gradually decreases from distal to proximal, the implant member having a hollow interior cavity dimensioned to accommodate bone growth inducing substances and a plurality of apertures extending through an external wall portion thereof in communication with the interior cavity to thereby permit bone ingrowth to facilitate fusion of one or more bone structures, the distal end portion defining an entry end surface, the entry end surface being closed to facilitate insertion relative to one or more bone structures.

10. The apparatus according to claim 9 wherein the external wall portion includes at least one flute formed in the threaded portion.

11. The apparatus according to claim 10 wherein the one flute extends to the entry end surface.

12. The apparatus according to claim 10 including a plurality of flutes formed in the threaded portion.

13. The apparatus according to claim 9 wherein the apertures are configured and dimensioned to provide immediate contact between the one or more bone structures and bone growth inducing substances disposed in the interior cavity upon positioning of the implant member adjacent the one or more bone structures.

14. An apparatus for promoting fusion with one or more bone structures, comprising an implant member having proximal and distal end portions and defining a longitudinal axis, the implant member including at least a longitudinal portion extending along at least a major portion of the length of the implant member, the longitudinal portion defining a generally frusto-conical configuration whereby the cross-sectional dimension of the longitudinal portion gradually decreases from distal to proximal, the implant member including a hollow interior cavity dimensioned to accommodate bone growth inducing substances and having a plurality of apertures extending through an exterior wall portion thereof in communication with the interior cavity the exterior wall portion having a threaded portion to facilitate positioning adjacent the one or more bone structures, and at least one flute defined in the threaded portion and extending through the exterior wall portion in communication with the interior cavity.

15. An apparatus for promoting fusion with one or more bone structures, comprising an implant member having proximal and distal end portions and defining a longitudinal axis, the implant member including at least a longitudinal portion extending along at least a major portion of the length of the implant member, the longitudinal portion defining a generally tapered configuration whereby the cross-sectional dimension of the longitudinal portion gradually decreases from distal to proximal, the implant member further including a second longitudinal portion disposed proximal of the first mentioned longitudinal portion, the second longitudinal portion defining a cylindrical configuration having a cross-sectional dimension which remains constant throughout the length of the second longitudinal portion.

16. An apparatus for facilitating fusion of adjacent vertebrae comprising an elongated implant member configured and dimensioned for insertion within an intervertebral space defined between adjacent vertebrae, the implant member having proximal and distal end portions and defining a longitudinal axis, the implant member including at least a longitudinal section extending along at least a major section of the length thereof, the longitudinal section defining a generally frusto-conical configuration whereby the cross-sectional dimension of the longitudinal section decreases from distal to proximal, the implant member including an internal cavity for accommodating bone growth inducing substances and having a plurality of apertures extending through an external wall portion thereof in communication with the internal cavity, the distal end portion having a closed entry end surface to prevent access to the internal cavity through the entry end surface.

17. The apparatus according to claim 16 wherein the implant member includes an external threaded portion for facilitating insertion within the intervertebral space.

18. The apparatus according to claim 17 wherein the implant member includes at least one flute, the one flute being formed in the threaded portion.

19. The apparatus according to claim 18 including at least one flute formed in the entry end surface.

20. The apparatus according to claim 19 further including an end cap mountable to the proximal end portion of the implant member to enclose the internal cavity.

21. The apparatus according to claim 16 wherein the apertures are configured and dimensioned to provide immediate contact between the one or more bone structures and bone growth inducing substances disposed in the interior cavity upon positioning of the implant member adjacent the one or more bone structures.

22. A fusion cage (1) for promoting fusion between two spaced apart vertebral bone structures which have posterior sections and anterior sections with a posterior interspace defined between the posterior sections and an anterior interspace defined between the anterior sections, and (2) for achieving a desired lordosis as the fusion cage is implanted by urging the fusion cage from the posterior sections toward the anterior sections using an posterior approach, the fusion cage comprising a cage body having a proximal end portion and a distal end portion, the cage body defining a generally frusto-conical configuration whereby the cross-sectional dimension of the cage body gradually decreases from the distal end portion to the proximal end portion, the distal end portion positionable in the posterior interspace between the posterior sections of the vertebral bone structures and with the proximal end portion positionable in the anterior interspace between the anterior sections of the vertebral bone structures as the cage body is urged using a posterior approach from an initial position where the distal end portion is positioned adjacent to the posterior sections to a final position where the distal end portion is positioned in the anterior interspace and the proximal end portion is positioned in the posterior interspace, the distal end portion defining a closed entry end surface.

23. The fusion cage of claim 22 wherein the cage body includes an external surface portion having a threaded portion to facilitate positioning between the vertebral bone structure.

24. The fusion cage of claim 22 wherein the cage body includes an internal cavity dimensioned to accommodate bone growth inducing structures.

25. The fusion cage of claim 24 wherein the cage body includes an external wall portion having a plurality of apertures extending therethrough in communication with the internal cavity.

26. The fusion cage of claim 25 wherein the proximal end portion of the cage body includes a trailing end, the trailing end having an opening in communication with the interior cavity.

27. The fusion cage of claim 26 including an end cap releasably mounted to the trailing end of the cage body to enclose the interior cavity.

28. A fusion cage (1) for promoting fusion between two spaced apart vertebral bone structures which have posterior sections and anterior sections with a posterior interspace defined between the posterior sections and an anterior interspace defined between the anterior sections, and (2) for achieving a desired lordosis as the fusion cage is implanted by urging the fusion cage from the posterior sections toward the anterior sections using an posterior approach, the fusion cage comprising a cage body having a proximal end portion and a distal end portion, the cage body defining a generally frusto-conical configuration whereby the cross-sectional dimension of the cage body gradually decreases from the distal end portion to the proximal end portion, the distal end portion positionable in the posterior interspace between the posterior sections of the vertebral bone structures and with the proximal end portion positionable in the anterior interspace between the anterior sections of the vertebral bone structures as the cage body is urged using a posterior approach from an initial position where the distal end portion is positioned adjacent to the posterior sections to a final position where the distal end portion is positioned in the anterior interspace and the proximal end portion is positioned in the posterior interspace the distal end portion defining a closed rounded entry end surface to facilitate insertion between the vertebral bone structures.

29. In combination:
an implant member for promoting fusion of one or more bone structures, the implant member having proximal and distal end portions and defining a longitudinal axis, the implant member including at least a longitudinal section defining a generally tapered configuration whereby the cross-sectional dimension of the longitudinal section decreases from distal to proximal, the implant member including an internal cavity for accommodating bone growth inducing substances and having a plurality of apertures extending through an external wall portion thereof in communication with the internal cavity, and an end cap mountable to the proximal end portion of the implant member to enclose the internal cavity; and an insertion tool to facilitate insertion of the implant member, the insertion tool including an elongated member having a remote end, the remote end including a tang to be received in a corresponding indentation of the implant member and a threaded shaft to be accommodated in a threaded bore of the end cap.

30. A method for fusion of adjacent vertebrae having posterior and anterior section comprising the steps:

providing a fusion implant member including proximal and distal ends and defining a longitudinal axis, the implant member including at least a longitudinal section defining a generally tapered configuration whereby the cross-sectional dimension of the longitudinal section decreases from distal to proximal;

accessing the intervertebral space defined between adjacent vertebrae from a posterior location;

inserting the distal end of the implant member within the intervertebral space from the posterior location and advancing the implant member such that the distal end and the proximal end of the implant member are adjacent respective anterior and posterior sections of the adjacent vertebrae; and permitting bone growth into contacting surfaces of the implant member to facilitate fusion of the adjacent vertebrae.

31. The method according to claim 30 including the step of introducing bone growth inducing substances within an internal cavity defined within the implant member whereby the adjacent vertebrae communicates with the bone growth inducing substances to form a solid fusion.

32. The method of claim 31 wherein the implant member includes an exterior wall portion having apertures extending therethrough wherein the step of permitting bone ingrowth includes permitting bony tissue of the adjacent vertebrae to grow through the apertures to communicate with the bone growth inducing substances.

33. The method of claim 32 wherein the implant member includes an external threaded portion, wherein the step of inserting includes rotating the implant member about the longitudinal axis such that the threaded portion engages the adjacent vertebrae to facilitate advancement of the implant member within the intervertebral space.

34. The method of claim 33 wherein the external threaded portion of the implant body includes a cutting thread wherein the step of inserting includes rotating the implant member whereby the cutting thread deburs bone tissue to self-tap the implant member within the intervertebral space.

35. The method of claim 30 wherein the implant member includes a second longitudinal section disposed proximal of the first-mentioned longitudinal section, the second longitudinal section defining a general cylindrical configuration having a cross-sectional dimension remaining substantially constant throughout the length of the second longitudinal section, and wherein the step of inserting includes advancing the implant member such that the second longitudinal portion is adjacent the posterior sections of the vertebrae.

36. An apparatus for facilitating fusion of adjacent vertebrae comprising an elongated implant member configured and dimensioned for insertion within an intervertebral space defined between adjacent vertebrae, the implant member having proximal and distal ends and defining a longitudinal axis, the implant member including at least a longitudinal section defining a generally tapered configuration whereby the cross-sectional dimension of the longitudinal section decreases from distal to proximal, the implant member including an internal cavity for accommodating bone growth inducing substances and having a plurality of apertures extending through an external wall portion thereof in communication with the internal cavity, the proximal end having an opening to permit access to the internal cavity to facilitate loading of the bone growth inducing substances therewithin, and an end cap releasably mounted to the proximal end.

37. The apparatus according to claim 36 wherein the longitudinal section is dimensioned to extend along a major portion of the length of the implant member.

38. The apparatus according to claim 37 wherein the longitudinal section defines a generally frusto-conical configuration.

39. The apparatus according to claim 36 wherein the end cap is dimensioned to substantially close the opening in the proximal end of the implant member.

40. The apparatus according to claim 36 wherein the distal end defines a closed entry end surface.

* * * * *